(12) United States Patent
Oral et al.

(10) Patent No.: US 8,501,686 B2
(45) Date of Patent: Aug. 6, 2013

(54) METHOD OF TREATING FATTY LIVER DISEASES AND CONDITIONS IN NON-LIPODYSTROPHIC SUBJECTS

(75) Inventors: Elif A. Oral, Ann Arbor, MI (US); Charles F. Burant, Ann Arbor, MI (US); Thomas L. Chenevert, Ann Arbor, MI (US); Hero K. Hussain, Ann Arbor, MI (US); Barbara J. McKenna, Ann Arbor, MI (US)

(73) Assignee: University of Michigan, Ann Arbor, MI (US)

(*) Notice: Subject to any disclaimer, the term of this patent is extended or adjusted under 35 U.S.C. 154(b) by 15 days.

(21) Appl. No.: 12/995,842

(22) PCT Filed: Jun. 5, 2009

(86) PCT No.: PCT/US2009/046458
§ 371 (c)(1),
(2), (4) Date: May 5, 2011

(87) PCT Pub. No.: WO2009/149379
PCT Pub. Date: Dec. 10, 2009

(65) Prior Publication Data
US 2011/0212889 A1    Sep. 1, 2011

Related U.S. Application Data

(60) Provisional application No. 61/059,258, filed on Jun. 5, 2008.

(51) Int. Cl.
*A61K 38/22* (2006.01)
*A61P 3/06* (2006.01)

(52) U.S. Cl.
USPC ............................................. 514/5.8; 530/350

(58) Field of Classification Search
None
See application file for complete search history.

(56) References Cited

U.S. PATENT DOCUMENTS

| | | | |
|---|---|---|---|
| 5,521,283 A | 5/1996 | DiMarchi et al. |
| 5,532,336 A | 7/1996 | DiMarchi et al. |
| 5,552,522 A | 9/1996 | DiMarchi et al. |
| 5,552,523 A | 9/1996 | Basinski et al. |
| 5,552,524 A | 9/1996 | Basinski et al. |
| 5,935,810 A | 8/1999 | Friedman et al. |
| 6,001,968 A | 12/1999 | Friedman et al. |
| 6,350,730 B1 | 2/2002 | Friedman et al. |
| 6,420,339 B1 | 7/2002 | Gegg et al. |
| 6,429,290 B1 | 8/2002 | Friedman et al. |
| 6,541,033 B1 | 4/2003 | Shah |
| 6,936,439 B2 | 8/2005 | Mann et al. |
| 7,112,659 B2 | 9/2006 | Mann et al. |
| 7,183,254 B2 | 2/2007 | DePaoli et al. |
| 7,208,577 B2 | 4/2007 | Pelleymounter et al. |
| 2005/0020496 A1 | 1/2005 | DePaoli et al. |
| 2005/0163799 A1 | 7/2005 | Mann et al. |
| 2005/0176107 A1 | 8/2005 | Pelleymounter et al. |

FOREIGN PATENT DOCUMENTS

| | | |
|---|---|---|
| WO | WO-96/05309 A2 | 2/1996 |
| WO | WO-96/40912 A1 | 12/1996 |
| WO | WO-97/06816 A1 | 2/1997 |
| WO | WO-97/18833 A1 | 5/1997 |
| WO | WO-97/38014 A1 | 10/1997 |
| WO | WO-98/08512 A1 | 3/1998 |
| WO | WO-98/28427 A1 | 7/1998 |
| WO | WO-98/46257 A1 | 10/1998 |
| WO | WO-00/09165 A1 | 2/2000 |
| WO | WO-00/20872 A1 | 4/2000 |
| WO | WO-00/21574 A2 | 4/2000 |
| WO | WO-00/47741 A1 | 8/2000 |
| WO | WO-2008/048691 A2 | 4/2008 |

OTHER PUBLICATIONS

Dixon et al., Gastroenterology, 121: 91-100, 2001.*
Agrawal et al., Management of nonalcoholic steatohepatitis: An analytic review. *J. Clin. Gastroenterol.* 35:253-61 (2002).
Asilmaz et al., Site and mechanism of leptin action in a rodent form of congenital lipodystrophy. *J. Clin. Invest.* 113:414-24 (2004).
Atzel et al., Mechanism of microsomal triglyceride transfer protein catalyzed lipid transport. Biochemistry 32:10444-50 (1993).
Beard et al., The insulin sensitivity index in nondiabetic man. Correlation between clamp-derived and IVGTT-derived values. *Diabetes* 35:362-9 (1986).
Benoist et al., Microsomal triacylglycerol transfer protein prevents presecretory degradation of apolipoprotein B-100. A dithiothreitol-sensitive protease is involved. *Eur. J. Biochem.* 240:713-20 (1996).
Bernard et al., Association between microsomal triglyceride transfer protein gene polymorphism and the biological features of liver steatosis in patients with type II diabetes. *Diabetologia* 43:995-9 (2000).
Brown et al., Sterol regulatory element binding proteins (SREBPs): controllers of lipid synthesis and cellular uptake. *Nutr. Rev.* 56:S1-S3 (1998).
Browning et al., Molecular mediators of hepatic steatosis and liver injury. *J. Clin. Invest.* 114:147-52 (2004).
Browning et al., Prevalence of hepatic steatosis in an urban population in the United States: Impact of ethnicity. *Hepatology* 40:1387-95 (2004).
Brunt et al., Nonalcoholic steatohepatitis: a proposal for grading and staging the histological lesions. *Am. J. Gastroenterol.* 94:2467-74 (1999).

(Continued)

*Primary Examiner* — Gyan Chandra
(74) *Attorney, Agent, or Firm* — Marshall, Gerstein & Borun LLP

(57) ABSTRACT

The invention generally relates to the use of leptin in the treatment of a leptin-responsive disease or condition in a non-lipodystrophic subject. More particularly, the invention is directed to the use of leptin in the treatment of a fatty liver disease in a non-lipodystrophic subject with a relative leptin deficiency. The invention includes methods for the treatment of nonalcoholic steatohepatitis (NASH), alcoholic fatty liver disease (AFLD), and nonalcoholic fatty liver disease (NAFLD) in a non-lipodystrophic subject. The invention includes the treatment of conditions ranging from ectopic lipid accumulation (steatosis) to cirrhosis.

10 Claims, 16 Drawing Sheets

OTHER PUBLICATIONS

Brunt, Nonalcoholic steatohepatitis: definition and pathology. *Semin. Liver Dis.* 21:3-16 (2001).

Chalasani et al., Does leptin play a role in the pathogenesis of human nonalcoholic steatohepatitis? *Am. J. Gastroenterol.* 98:2771-6 (2003).

Chao et al., Adipose tissue is required for the antidiabetic, but not for the hypolipidemic, effect of thiazolidinediones. *J. Clin. Invest.* 106:1221-8 (2000).

Chitturi et al., Serum leptin in NASH correlates with hepatic steatosis but not fibrosis: A manifestation of lipotoxicity? *Hepatology* 36:403-9 (2002).

Cohen et al., Role for stearoyl-CoA desaturase-1 in leptin-mediated weight loss. *Science* 297:240-3 (2002).

Cohen et al., Selective deletion of leptin receptor in neurons leads to obesity. *J. Clin. Invest.* 108:1113-21 (2001).

Colombo et al., Transplantation of adipose tissue lacking leptin is unable to reverse the metabolic abnormalities associated with lipoatrophy. *Diabetes* 51:2727-33 (2002).

Considine et al., Serum immunoreactive-leptin concentrations in normal-weight and obese humans. *N. Engl. J. Med.* 334:292-5 (1996).

Day et al., The biochemistry of alcohol-induced fatty liver. *Biochim. Biophys. Acta.* 1215:33-48 (1994).

Day, Non-alcoholic steatohepatitis (NASH): where are we now and where are we going? *Gut* 50:585-8 (2002).

de Almeida et al., Plasma total and free fatty acids composition in human non-alcoholic steatohepatitis. *Clin. Nutr.* 21:219-23 (2002).

de Fourmestraux et al., Transcript profiling suggests that differential metabolic adaptation of mice to a high fat diet is associated with changes in liver to muscle lipid fluxes. *J. Biol. Chem.* 279:50743-53 (2004).

de Knegt, Non-alcoholic steatohepatitis: clinical significance and pathogenesis. *Scand. J. Gastroenterol. Suppl.*: 234:88-92 (2001).

Diehl, Nonalcoholic steatohepatitis. *Semin. Liver Dis.* 19:221-9 (1999).

Flament et al., Drug development and industrial pharmacy. *Drug Development and Industrial Pharmacy* 21(20):2263-2285 (1995).

Fowler et al., Validation of the in vivo measurement of adipose tissue by magnetic resonance imaging of lean and obese pigs. *Am. J. Clin. Nutr.* 56:7-13 (1992).

Gavrila et al., Serum adiponectin levels are inversely associated with overall and central fat distribution but are not directly regulated by acute fasting or leptin administration in humans: cross-sectional and interventional studies. *J. Clin. Endocrinol. Metab.* 88:4823-31 (2003).

Gavrilova et al., Surgical implantation of adipose tissue reverses diabetes in lipoatrophic mice. *J. Clin. Invest.* 105:271-8 (2000).

Giannini et al., Leptin levels in nonalcoholic steatohepatitis and chronic hepatitis C. *Hepatogastroenterology* 46:2422-5 (1999).

Grundy et al., Implications of recent clinical trials for the National Cholesterol Education Program Adult Treatment Panel III guidelines. *Circulation* 110:227-39 (2004).

Grunnet et al., Effect of ethanol on lipid metabolism in cultured hepatocytes. *Biochem. J.* 228:673-81 (1985).

Haarbo et al., Validation of body composition by dual energy X-ray absorptiometry (DEXA). *Clin. Physiol.* 11:331-41 (1991).

Halaas et al., Physiological response to long-term peripheral and central leptin infusion in lean and obese mice. *Proc. Natl. Acad. Sci. U.S.A.* 94:8878-83 (1997).

Heymsfield et al., Recombinant leptin for weight loss in obese and lean adults: a randomized, controlled, dose-escalation trial. *JAMA* 282:1568-75 (1999).

James et al., Non-alcoholic steatohepatitis: Another disease of affluence. *Lancet* 353:1634-6 (1999).

James et al., Molecular basis of the hepatic control of cholesterol metabolism. *Nutr. Rev.* 56(2): S54-S75 (1998).

Javor et al., Leptin reverses nonalcoholic steatohepatitis in patients with severe lipodystrophy. *Hepatology* 41:753-60 (2005).

Kim et al., Mechanism of insulin resistance in A-ZIP/F-1 fatless mice. *J. Biol. Chem.* 275:8456-60 (2000).

Kleiner et al., Design and validation of a histological scoring system for nonalcoholic fatty liver disease. *Hepatology* 41:1313-21 (2005).

Kuczmarski et al., Varying body mass index cutoff points to describe overweight prevalence among U.S. adults: NHANES III (1988 to 1994). *Obes. Res.* 5:542-8 (1997).

Le et al., Serum leptin levels, hepatic leptin receptor transcription, and clinical predictors of non-alcoholic steatohepatitis in obese bariatric surgery patients. *Surg. Endosc.* 21:1593-9 (2007).

Lee et al., PPAR alpha is necessary for the lipopenic action of hyperleptinemia on white adipose and liver tissue. *Proc. Natl. Acad. Sci. U.S.A.* 99:11848-53 (2002).

Liangpunsakul et al., Treatment of Nonalcoholic Fatty Liver Disease. *Curr. Treat. Options Gastroenterol.* 6:455-63 (2003).

Lin et al., Metformin reverses fatty liver disease in obese, leptin-deficient mice. *Nat. Med.* 6:998-1003 (2000).

Ludwig et al., Nonalcoholic steatohepatitis: Mayo Clinic experiences with a hitherto unnamed disease. *Mayo Clin. Proc.* 55:434-8 (1980).

Ludwig et al., Review: nonalcoholic steatohepatitis. *J. Gastroenterol. Hepatol.* 12:398-403 (1997).

Malcolmson et al., Dry powder formulations for pulmonary delivery. *PSTT* 1(9):394-8 (1998).

Marchesini et al., Metformin in non-alcoholic steatohepatitis. *Lancet* 358:893-4 (2001).

Matsusue et al., Liver-specific disruption of PPARgamma in leptin-deficient mice improves fatty liver but aggravates diabetic phenotypes. *J. Clin. Invest.* 111:737-47 (2003).

Matteoni et al., Nonalcoholic fatty liver disease: a spectrum of clinical and pathological severity. *Gastroenterol.* 116:1413-9 (1999).

Matthews et al., Homeostasis model assessment: insulin resistance and beta-cell function from fasting plasma glucose and insulin concentrations in man. *Diabetologia* 28: 412-9 (1985).

McCullough, Update on nonalcoholic fatty liver disease. *J. Clin. Gastroenterol.* 34:255-62 (2002).

Minokoshi et al., Role of AMP-activated protein kinase in leptin-induced fatty acid oxidation in muscle. *Biochem. Soc. Trans.* 31:196-201 (2003).

Munzberg et al., Leptin receptor action and mechanisms of leptin resistance. *Cell. Mol. Life Sci.* 62:642-52 (2005).

Nehra et al., Nutritional and metabolic considerations in the etiology of nonalcoholic steatohepatitis. *Dig. Dis. Sci.* 46:2347-52 (2001).

Neuschwander-Tetri et al., Improved nonalcoholic steatohepatitis after 48 weeks of treatment with the PPAR-gamma ligand rosiglitazone. *Hepatology* 38:1008-17 (2003).

Neuschwander-Tetri et al., Interim results of a pilot study demonstrating the early effects of the PPAR-gamma ligand rosiglitazone on insulin sensitivity, aminotransferases, hepatic steatosis and body weight in patients with non-alcoholic steatohepatitis. *J. Hepatol.* 38:434-40 (2003).

Ntambi, Regulation of stearoyl-CoA desaturase by polyunsaturated fatty acids and cholesterol. *J. Lipid Res.* 40:1549-58 (1999).

Oral et al., Leptin-replacement therapy for lipodystrophy. *N. Engl. J. Med.* 346:570-8 (2002).

Oral, Lipoatrophic diabetes and other related syndromes. *Rev. Endocrin. Metab. Disord.* 4:61-77 (2003).

Petersen et al., Leptin reverses insulin resistance and hepatic steatosis in patients with severe lipodystrophy. *J. Clin. Invest.* 109:1345-50 (2002).

Petersen et al., Reversal of nonalcoholic hepatic steatosis, hepatic insulin resistance, and hyperglycemia by moderate weight reduction in patients with type 2 diabetes. *Diabetes* 54:603-8 (2005).

Promrat et al., A pilot study of pioglitazone treatment for nonalcoholic steatohepatitis. *Hepatology* 39:188-96 (2004).

Reddy et al., Lipid metabolism and liver inflammation. II. Fatty liver disease and fatty acid oxidation. *Am. J. Physiol. Gastrointest. Liver Physiol.* 290:G852-8 (2006).

Reddy et al., Peroxisomal beta-oxidation and peroxisome proliferator-activated receptor alpha: an adaptive metabolic system. *Annu. Rev. Nutr.* 21:193-230 (2001).

Reitman et al., Lipoatrophy revisited. *Trends Endocrinol. Metab.* 11:410-6 (2000).

Ruhl et al., Leptin concentrations in the United States: relations with demographic and anthropometric measures. *Am. J. Clin. Nutr.* 74:295-301 (2001).

Sabuncu et al., The effects of sibutramine and orlistat on the ultrasonographic findings, insulin resistance and liver enzyme levels in obese patients with non-alcoholic steatohepatitis. *Rom. J. Gastroenterol.* 12:189-92 (2003).

Samuel et al., Mechanism of hepatic insulin resistance in non-alcoholic fatty liver disease. *J. Biol. Chem.* 279:32345-53 (2004).

Scheen et al., Obesity and liver disease. *Best Pract. Res. Clin. Endocrinol. Metab.* 16:703-16 (2002).

Shadid et al., Effect of pioglitazone on biochemical indices of non-alcoholic fatty liver disease in upper body obesity. *Clin. Gastroenterol. Hepatol.* 1:384-7 (2003).

Shimomura et al., Decreased IRS-2 and increased SREBP-1c lead to mixed insulin resistance and sensitivity in livers of lipodystrophic and ob/ob mice. *Mol. Cell.* 6:77-86 (2000).

Shimomura et al., Increased levels of nuclear SREBP-1c associated with fatty livers in two mouse models of diabetes mellitus. *J. Biol. Chem.* 274:30028-32 (1999).

Shimomura et al., Insulin resistance and diabetes mellitus in transgenic mice expressing nuclear SREBP-1c in adipose tissue: model for congenital generalized lipodystrophy. *Genes Dev.* 12:3182-94 (1998).

Shimomura et al., Leptin reverses insulin resistance and diabetes mellitus in mice with congenital lipodystrophy. *Nature* 401:73-6 (1999).

Sparti et al., Relationship between resting metabolic rate and the composition of the fat-free mass. *Metabolism* 46:1225-30 (1997).

Takahashi et al., Plasma leptin levels and body fat distribution. *Horm. Metab. Res.* 28:751-2 (1996).

Taylor et al., Syndromes associated with insulin resistance and acanthosis nigracans. *J. Basic Clin. Physiol. Pharmacol.* 9:419-39 (1998).

Unger et al., Regulation of fatty acid homeostasis in cells: novel role of leptin. *Proc. Natl. Acad. Sci. U.S.A.* 96:2327-32 (1999).

Unger, Lipotoxicity in the pathogenesis of obesity-dependent NIDDM. Genetic and clinical implications. *Diabetes* 44:863-70 (1995).

Uygun et al., Serum leptin levels in patients with nonalcoholic steatohepatitis. *Am. J. Gastroenterol.* 95:3584-9 (2000).

Venkatesan et al., Effect of chronic ethanol feeding on the hepatic secretion of very-low-density lipoproteins. *Biochim. Biophys. Acta.* 960:61-6 (1988).

Vigouroux et al., Diabetes, insulin resistance and dyslipidaemia in lipodystrophic HIV-infected patients on highly active antiretroviral therapy (HAART). *Diabetes Metab.* 25(3):225-32 (1999).

Wang et al., Novel form of lipolysis induced by leptin. *J. Biol. Chem.* 274:17541-4 (1999).

Wu et al., Mechanisms controlling mitochondrial biogenesis and respiration through the thermogenic coactivator PGC-1. *Cell* 98:115-24 (1999).

Yu et al., Adipocyte-specific gene expression and adipogenic steatosis in the mouse liver due to peroxisome proliferator-activated receptor gamma1 (PPARgamma1) overexpression. *J. Biol. Chem.* 278:498-505 (2003).

International Search Report and Written Opinion of the International Searching Authority, PCT/US2009/046458, Korean Intellectual Property Office, dated Feb. 10, 2010.

International Preliminary Report on Patentability, PCT/US2009/046458, dated Dec. 6, 2010.

\* cited by examiner

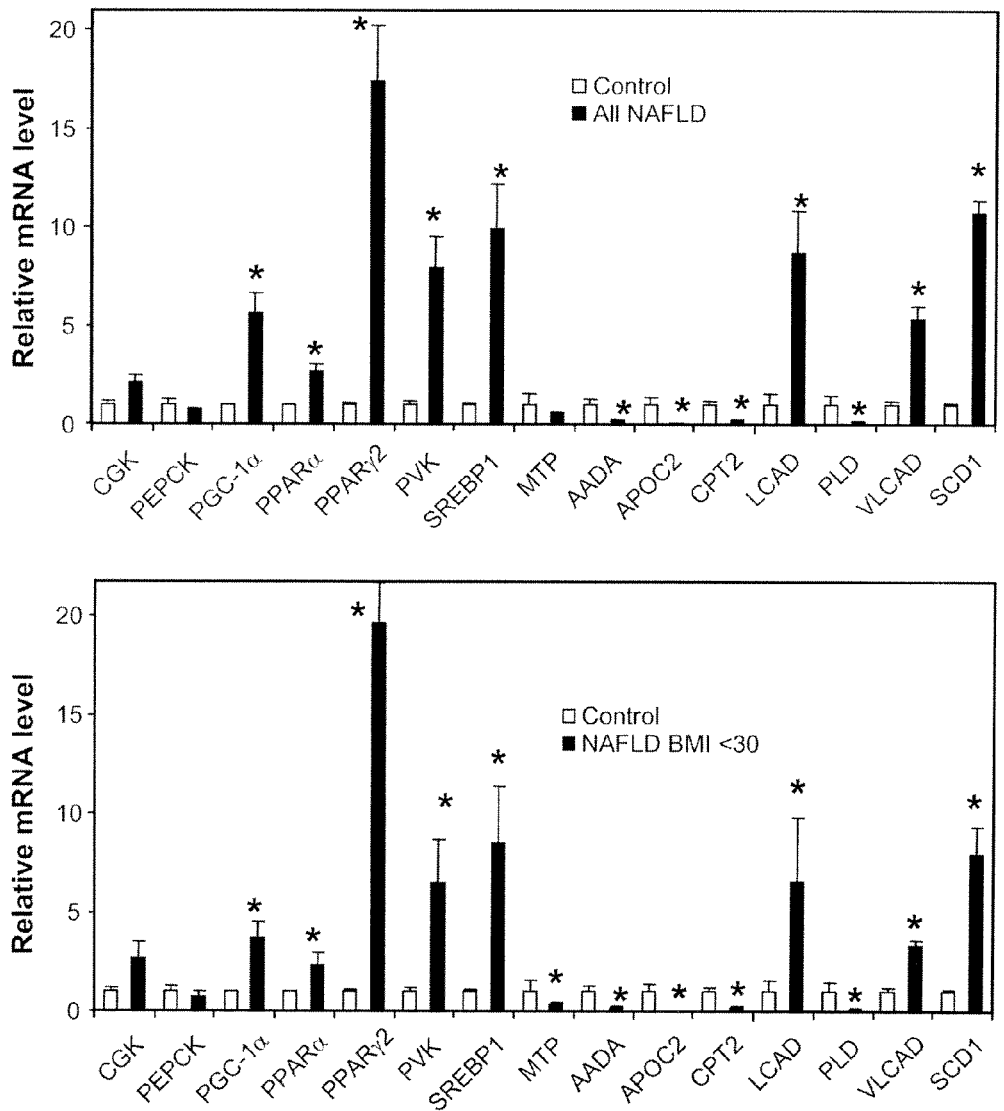

CGK=glucokinase; PEPCK=phosphoenoyl pyruvate kinase; PGC-1α=PPARγ coactivator 1; PPAR=Peroxisomal proliferator activated receptors α an γ; PVK=pyruvate kinase; SREBP-1c=sterol regulatory element binding protein-1c; MTP=microsomal transfer protein; AADA=arylacetaminde deacetylase; APOC2=apolipoprotein C2; CPT2=carnitine palmitoyl transferase II; LCAD and VLCAD=long chain and very long chain acyl-CoA dehydrogenase; PLD=phospholipase D1; SCD-1= stearoyl-CoA desaturase.

Figure 3

| Ingenuity Cannonical Pathways | -Log(P-value) | Molecules |
|---|---|---|
| Glutamate Receptor Signaling | 2.14E00 | GRM2,CALM3, SLC17A1, SLC1A2, GNG7 |
| VEGF Signaling | 2.04E00 | PIK3CA, VEGFB (includes EG:7423), FOXO1, MRAS, VEGFC, VCL |
| Insulin Receptor Signaling | 1.79E00 | PIK3CA, ACCN1, FOXO1, TSC2, INS, MRAS, PRKAR2A |
| Nitric Acid Signaling in the Cardiovascular System | 1.74E00 | PIK3CA, CALM3, VEGFB (includes EG:7423), PRKAR2A, VEGFC |
| Inositol Metabolism | 1.55E00 | VCL, ADI1 |
| Urea Cycle and Metabolism of Amino Groups | 1.48E00 | SARDH, AGMAT, PYCR2 |
| FXR/RXR Activation | 1.43E00 | PON1, FOXO1, NR1H4, FOXA1, INS |
| Amyotrophic Lateral Sclerosis Signaling | 1.38E00 | PIK3CA, VEGFB (includes EG:7423), SLC1A2, VEGFC, ALS2 |
| IGF-1 Signaling | 1.38E00 | PIK3CA, FOXO1, MRAS, PRKAR2A, CYR61 |

Figure 14A

SEQUENCE LISTING

<160> NUMBER OF SEQ ID NOS: 1

<210> SEQ ID NO 1
<211> LENGTH: 147
<212> TYPE: PRT
<213> ORGANISM: Homo sapiens

<400> SEQUENCE: 1

```
Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
```

```
                    115                 120                 125
Arg Leu Gln Gly Ser Leu Gln Asp Met Leu Trp Gln Leu Asp Leu Ser
                130                 135                 140

Pro Gly Cys
145
```

METHOD OF TREATING FATTY LIVER DISEASES AND CONDITIONS IN NON-LIPODYSTROPHIC SUBJECTS

GOVERNMENT RIGHTS

This invention was made with government support under Grant No. NIDDK-RO-3DK074488 awarded by the National Institutes of Health. The government has certain rights in the invention.

FIELD OF THE INVENTION

The invention generally relates to methods and compositions for the treatment of fatty liver conditions in non-lipodystrophic subjects. Such conditions include a spectrum of alcoholic fatty liver disease (AFLD) and nonalcoholic fatty liver disease (NAFLD) that range from ectopic lipid accumulation (steatosis) to cirrhosis. More particularly, the invention is directed to methods of treating nonalcoholic steatohepatitis (NASH) in non-lipodystrophic subjects comprising administering to the subjects an effective amount of a composition comprising leptin. In addition, the invention relates to methods of treating fatty liver conditions in non-lipodystrophic patients with relatively low leptin levels by administering a composition comprising leptin. The invention also relates to uses of leptin for the treatment of any condition associated with fatty liver.

BACKGROUND OF THE INVENTION

Obesity and insulin resistance afflict millions of Americans. Data from the National Health and Nutrition Survey, cycle III 1988-94, (NHANES III) suggests that there is in excess of 23% of Americans who are obese (Kuczmarski et al., *Obes. Res.* 5:542-548, 1997). At least a similar number of individuals are known to be overweight. This large epidemic results in increased mortality and morbidity from cardiovascular disease and Type 2 diabetes (Grundy et al., Circulation 110:227-239, 2004). Among emerging co-morbidities of obesity and insulin resistance is a condition called nonalcoholic fatty liver disease (NAFLD) (Liangpunsakul et al., *Curr. Treat. Options Gastroenterol.* 6:455-463, 2003). Nonalcoholic fatty liver disease is characterized by macrovesicular steatosis of the liver occurring in individuals who consume little or no alcohol. The histological spectrum of NAFLD includes the presence of steatosis alone, fatty liver and inflammation and a more aggressive form called nonalcoholic steatohepatitis (NASH), characterized by the presence of steatosis, inflammation and varying degrees of fibrosis (Brunt et al., *Am. J. Gastroenterol.* 94:2467-2474, 1999; Brunt, *Semin. Liver Dis.* 21:3-16, 2001). NASH can progress into cirrhosis and permanent liver failure (Brunt et al., supra, 1999; Brunt, supra, 2001; Ludwig et al., *J. Gastroenterol. Hepatol.* 12:398-403, 1997).

The lack of symptoms in the early stages and the absence of uniform diagnostic criteria make it difficult to determine the true prevalence of NAFLD and its various forms. Data from an autopsy study in Canada found that roughly 20% of obese individuals have hepatic steatosis (Scheen et al., *Best Pract. Res. Clin. Endocrinol. Metab.* 16:703-716, 2002). More recently, a landmark study of NMR spectroscopy carried out on the population of the Dallas Heart study, indicated that more than a third of the study population, a sedentary urban United States population comprising 2,349 patients with an excellent representation of different sexes, races and ethnic groups, had hepatic steatosis (Browning et al., *Hepatology* 40:1387-1395, 2004). The rate of observing the aggressive form NASH is not known in this population, but about ⅕ of these patients are predicted to have NASH if they were subjected to a biopsy (McCullough, *J. Clin. Gastroenterol.* 34:255-262, 2002). Thus, NASH is estimated to be prevalent at a rate of at least 5% of the general population.

Nonalcoholic steatohepatitis (NASH) lies on a spectrum of nonalcoholic fatty liver disease (NAFLD) that ranges from ectopic lipid accumulation (steatosis) to cirrhosis (Matteoni et al., *Gastroenterol.* 116:1413-1419, 1999). Steatosis is believed to sensitize the liver to metabolic injury leading to inflammation, necrosis, and fibrosis (James et al., *Lancet* 353:1634-1636, 1999; Ludwig et al., *Mayo Clin. Proc.* 55:434-438, 1980; Day, *Gut* 50:585-588, 2002; Browning et al., *J. Clin. Invest.* 114:147-152, 2004). Thus, steatosis is a constant feature of NASH, but NASH is only distinguishable by liver biopsy. The assessment and severity of NASH is made histologically based on the patterns and degrees of hepatic steatosis, inflammation, and injury and, by definition, occurs only in the absence of significant alcohol consumption (Brunt, supra, 2001). While steatosis is seen in both animal and human models, NASH is only fully appreciated in the human condition (Browning et al., supra, 2004). Thus, understanding the clinical variation observed in NASH is critical for the development of therapeutic strategies for this condition.

NASH is now accepted as a progressive metabolic liver disease. Hepatic fatty infiltration or steatosis is thought to be the precursor for NASH or the "first hit" to the liver in the development of this metabolic liver disease. Steatosis is believed to sensitize the liver to subsequent metabolic injury leading to inflammation, necrosis, and fibrosis (James et al., supra, 1999; Ludwig et al., supra, 1980; Day, supra, 2002; Browning et al., supra, 2004). The liver plays a key role in both glucose and lipid metabolism. Several important studies suggested that insulin resistance was a key feature of hepatic steatosis (de Knegt, *Scand. J. Gastroenterol.* Suppl.: 88-92, 2001). The engorgement of the liver with lipid causes severe insulin resistance in the liver and abnormal glucose production (Samuel et al., *J. Biol. Chem.* 279:32345-32353, 2004). Studies from rodents suggest that genes important for adipocyte differentiation (such as peroxisome proliferator-activated receptor gamma 1 (PPARg1), PPARg2, and SREBP-1) are up-regulated in steatotic livers (Brown et al., *Nutr. Rev.* 56:S1-S3; S54-S75, 1998; Matsusue et al., *J. Clin. Invest.* 111:737-747, 2003; Yu et al., *J. Biol. Chem.* 278:498-505, 2003). Furthermore, the presence of peripheral insulin resistance and hyperinsulinemia worsens the problem of increased lipid deposition in the liver, leading to a vicious metabolic cycle (Shimomura et al., *Mol. Cell.* 6:77-86, 2000). Hence, therapeutic interventions that decrease lipid deposition in the liver are likely to improve both insulin resistance and abnormal hepatic glucose production.

Data has been accumulating to support a "second hit" theory at play on top of lipid deposition in the pathogenesis of NASH (Diehl, Semin. Liver Dis. 19:221-229, 1999). The suspected second hit may be intracellular oxidative stress that can be induced by multiple mechanisms such as excess iron accumulation, endotoxin exposure, pro-inflammatory cytokines or other unknown factors. Accumulation of fatty acids and change of the balance of fatty acids may also be responsible for generation of increased free radicals by being a substrate for lipid peroxidation (de Almeida et al., *Clin. Nutr.* 21:219-223, 2002).

There is no standard therapy for management of NASH at this point (Agrawal et al., *J. Clin. Gastroenterol.* 35:253-261, 2002). The first line of medical intervention in obese patients is recommendation of weight loss and exercise (Nehra et al., *Dig. Dis. Sci.* 46:2347-2352, 2001). Short-term weight loss has been shown to improve insulin resistance, decrease visceral fat deposition and hepatic steatosis; however, its ultimate effect on histological improvement and the natural course of NASH is not known (Petersen et al., *Diabetes* 54:603-608, 2005). However, long-term adherence and success of this recommendation is questionable. Sibutramine and Orlistat have been reportedly associated with improved sonographic findings and insulin resistance (Sabuncu et al., *Rom. J. Gastroenterol.* 12:189-192, 2003). The most promising drugs thus far have been insulin sensitizers, like metformin (Lin et al., *Nat. Med.* 6:998-1003, 2000; Marchesini et al., *Lancet* 358:893-894, 2001) and thiazolidinediones rosiglitazone (Neuschwander-Tetri et al., *Hepatology* 38:1008-1017, 2003; Neuschwander-Tetri et al., *J. Hepatol.* 38:434-440, 2003. and pioglitazone (Shadid et al., *Clin. Gastroenterol. Hepatol.* 1:384-387, 2003; Promrat et al., *Hepatology* 39:188-196, 2004). Despite the encouraging results observed with these drugs, the need for additional new therapies is evident.

In rodent models, steatosis occurs with decreased leptin action, whether due to leptin deficiency or resistance (Lee et al., *Proc. Natl. Acad. Sci. U.S.A.* 99:11848-11853, 2002; Unger, *Diabetes* 44:863-870, 1995; Unger et al., *Proc. Natl. Acad. Sci. U.S.A.* 96:2327-2332, 1999; Wang et al., *J. Biol. Chem.* 274:17541-17544, 1999). Rodent models of leptin deficiency either have mutations in the ob gene encoding leptin (the ob/ob mouse) or they lack fat, the organ manufacturing leptin. Animal models lacking white adipose tissue have been engineered using a couple of different strategies. Regardless of the strategy, the deficiency of white adipose tissue leads to leptin deficiency, insulin resistance, severe hypertriglyceridemia and massive hepatic steatosis (Reitman et al., *Trends Endocrinol. Metab.* 11:410-416, 2000). Evaluation of insulin sensitivity in one of these models using a hyperinsulinemic euglycemic clamp demonstrated decreased hepatic insulin sensitivity, i.e. dysregulated hapatic glucose production (Kim et al., *J. Biol. Chem.* 275:8456-8460, 2000). Transplantation of fat from littermates, into this model resulted in amelioration of total body insulin sensitivity, dyslipidemia, hepatic steatosis and also hepatic glucose production in a dose dependent manner (Reitman et al., *Trends Endocrinol. Metab.* 11:410-416, 2000; Kim et al., *J. Biol. Chem.* 275:8456-8460, 2000, Gavrilova et al., *J. Clin. Invest.* 105:271-278, 2000). In contrast, if fat is procured from ob mice, the metabolic amelioration of fat transplantation is not observed (Colombo et al., *Diabetes* 51:2727-2733, 2002).

Shimomura et al, tested whether replacing leptin made an impact on the insulin sensitivity, dyslipidemia and hepatic steatosis in a model of fat deficiency. A major impact of physiological leptin replacement was evident after 3 weeks of therapy (Shimomura et al., *Genes Dev.* 12:3182-3194, 1998; Shimomura et al., *Nature* 401:73-76, 1999). Furthermore, this study showed that lipogenesis was dysregulated in the liver in the absence of leptin which was corrected with leptin replacement. Other reports confirmed the validity of these observations in other models. The observations related to the efficacy of leptin in the fatless mice formed the basis for our testing the efficacy of leptin replacement therapy in a human disease characterized by absence of body fat, namely lipodystrophy (Oral et al., *N. Engl. J. Med.* 346:570-578, 2002). In addition to displaying severe insulin resistance, dyslipidemia and hepatic steatosis, patients with generalized lipodystrophy also acquire NASH. In fact, cirrhosis and liver failure are important causes of premature death in these patients (Taylor et al., *J. Basic Clin. Physiol. Pharmacol.* 9:419-439, 1998; Oral, *Rev. Endocr. Metab. Disord.* 4:61-77, 2003). The preliminary results indicate that 4-months of leptin replacement was effective in reversing NASH in these patients in addition to causing significant improvements in metabolic parameters. Treatment with recombinant leptin has also been highly effective in the treatment of morbid obesity associated with congenital leptin deficiency. These patients also display a number of hormonal and metabolic abnormalities which respond to leptin therapy. To our knowledge, the liver histopathology that is associated with this human condition has not been described. Thus, whether leptin therapy leads to a beneficial therapeutic effect in the livers of these rare patients is not known.

While leptin therapy leads to a number of beneficial effects in conditions associated with leptin deficiency, the majority of human obesity is thought to be associated with leptin resistance. In rodents, leptin appears to exert a therapeutic effect in models of leptin resistance when sufficient amounts of the hormone are administered (Halaas et al., *Proc. Natl. Acad. Sci. U.S.A.* 94:8878-8883, 1997). In addition, central administration of leptin results in beneficial effects in many of the models of obesity (Halaas et al., supra). These observations had triggered significant enthusiasm for the development of recombinant leptin as a therapy for obesity. However, the obesity trials in humans indicated leptin resistance to be a more significant problem than in rodents. In a Phase II trial, obese subjects treated with leptin did not demonstrate statistically different amounts of weight loss compared to the placebo-treated subjects. Careful analyses of the presented data indicates the presence of at least 25% of patients with clinically meaningful and powerful responses producing weight loss of up to 16 kg (Heymsfield et al., *JAMA* 282:1568-1575, 1999). The parameters that distinguish responders from non-responders were not published. Since leptin has been clinically effective in states of leptin deficiency, one plausible hypothesis would be that the responders had relatively lower levels of leptin at baseline, indicating higher leptin sensitivity. However, such an analysis has not been provided from the Phase II trial. The studies exploring leptin's therapeutic potential in obesity did not evaluate the efficacy on liver histopathology. In addition, patients with abnormal liver function were specifically excluded from those studies.

As it is clear from evidence presented thus far, the question of leptin's role in the development of common forms of NASH in humans is not yet answered. The first step in determining the answer to this question is to determine what leptin levels are in NASH. The consensus from a handful of reports investigating this question is that leptin levels appear to be "elevated" as a mean compared to "healthy" normals (Chitturi et al., *Hepatology* 36:403-409, 2002; Uygun et al., *Am. J. Gastroenterol.* 95:3584-3589, 2000; Giannini et al., *Hepatogastroenterology* 46:2422-2425, 1999; Chalasani et al., *Am. J. Gastroenterol.* 98:2771-2776, 2003). However, it is hard to reach a conclusion from these reports for various reasons. First of all, two of these studies were done outside the United States and the leptin levels of the "control groups" were lower than the population normals published in the United States (Uygun et al., supra; Giannini et al., supra). Hence, their applicability or validity for the patients in the United States is unclear. Further, these studies, except for one (Chalasani et al, supra) did not evaluate regional body composition in terms of subcutaneous and visceral adipose tissue compartments (Chitturi et al., supra; Uygun et al., supra; Giannini et al., supra). Insulin resistance was not evaluated in relationship to body composition and leptin levels (Chitturi et al., supra; Uygun et al., supra; Giannini et al., supra). The differences between different BMI categories were not explored (Chitturi et al., supra; Uygun et al., supra; Giannini et al., supra). As indicated in the most recent paper (Chalasani et al, supra), the number of patients were limited, and one of the studies had only six patients with NASH (Giannini et al., supra). Comparisons of circulating leptin levels in patients with NASH with a so-called control group has been misleading since it is impossible to define a true control group without performing a liver biopsy (Chalasani et al, supra). Most importantly, leptin levels were not analyzed as the variable affecting other characteristics.

While studying and interpreting leptin levels, it is important to recognize that circulating leptin levels are a function of total body adiposity. Large epidemiological studies suggest that leptin levels correlate with body weight and BMI (Considine et al., *N. Engl. J. Med.* 334:292-295, 1996; Takahashi et al., *Horm. Metab. Res.* 28:751-752, 1996). The characteristics of body fat depots also play a contributory role in determining leptin levels. For example, subcutaneous fat is a more efficient producer of leptin (Takahashi et al., supra).

Based on the data from lipodystrophic patients and rodents collectively, it is hypothesized that circulating leptin level is an important signal in the modulation of the pathophysiology of lipid deposition in the liver. It is further hypothesized that a low leptin level plays an important role in communicating to the liver whether this organ should be utilized as a lipid storage site. When the storage capacity of adipose tissue is inherently low (which is associated with low leptin levels) or is beyond maximum capacity (associated with high leptin levels, but there is a state of leptin resistance), the liver takes on an additional role of "energy storage" and becomes engorged with fat. Fat deposition in humans makes the liver vulnerable to metabolic injury. This vulnerability develops into the clinical picture of NASH. In this paradigm, it is hypothesized that the patients with low leptin levels will respond to exogenous leptin therapy aiming to augment their leptin levels.

Leptin has clear anti-steatotic effects. The exact mechanisms of leptin's anti-steatotic effects in various tissues are not known. To elucidate the mechanism by which leptin reduces hepatic lipid content, Cohen et al, used microarrays to identify genes in liver that were differentially regulated by leptin or by food restriction (pair-feeding) (Cohen et al., *Science* 297:240-243, 2002). Leptin-treated ob/ob mice lose significantly more weight than pair-fed ob/ob mice, indicating that leptin stimulates energy expenditure. The authors identified 15 clusters of genes with distinct patterns of expression, six of which correspond to genes specifically regulated by leptin, but not by pair-feeding. To prioritize leptin-regulated genes for functional analysis, the authors then developed an algorithm to identify and rank genes that are specifically repressed by leptin. The gene encoding stearoyl-CoA desaturase (SCD-1) ranked the highest in this analysis. The microsomal enzyme SCD-1 is required for the biosynthesis of the monounsaturated fats palmitoleate and oleate from saturated fatty acids (Ntambi, *J. Lipid Res.* 40:1549-1558, 1999). SCD-1 RNA levels were markedly elevated in untreated ob/ob liver and these levels normalized with leptin treatment. Pair-fed mice showed a smaller and delayed decrease in SCD-1 gene expression. Also consistent with this observation, the authors noted that mice which carry mutations in SCD-1 had significantly reduced body fat mass. Furthermore, crossing leptin deficient ob/ob mice with the SCD-1 deficient mice produced a marked decrease in hepatic lipid content, size of the liver and a marked reduction in circulating serum triglyceride concentrations, effects similar to leptin treatment. These observations suggest that a significant proportion of leptin's metabolic effects may result from inhibition of SCD-1. Additionally, leptin increases hepatic and adipocyte expression of PPARγ coactivator (PGC)-1α 33, which regulates mitochondria biogenesis and fat oxidation (Wu et al., *Cell* 98:115-124, 1999).

Another important anti-steatotic effect of leptin was uncovered by studying muscle tissue. Minokoshi and colleagues showed that leptin selectively stimulates phosphorylation and activation of the α2 catalytic subunit of 5'AMP-activated protein kinase (AMPK) (α2 AMPK) in skeletal muscle, thus establishing a previously unknown signaling pathway for leptin (Minokoshi et al., *Biochem. Soc. Trans.* 31:196-201, 2003). In parallel with its activation of AMPK, leptin suppresses the activity of acetyl CoA carboxylase (ACC), thereby stimulating the oxidation of fatty acids in muscle. Whether leptin causes its peripheral effects via its central action or directly through its peripheral receptors is not known. For instance, the lipopenic action of leptin has been duplicated in rodents with small, centrally administered doses (Asilmaz et al., *J. Clin. Invest.* 113:414-424, 2004). The effect is achieved even with the knockout of peripheral leptin receptors (Cohen et al., *J. Clin. Invest.* 108:1113-1121, 2001), suggesting that leptin signals through one or more centrally-mediated intermediates, which in turn lead to increased fatty acid oxidation and suppression of lipogenesis.

Currently there are no good clinical markers that allow for the identification of patients with NASH. Similarly, there are no therapies to slow down or alter the course of further disease progression in NASH. Such markers and treatment for NASH are needed in the art. NASH ranks as one of the major causes of cirrhosis in America, behind hepatitis C and alcoholic liver disease. Thus, there exists a need in the art for methods of treating NASH. The invention provides recombinant leptin therapy for patients with NASH who demonstrate a leptin deficiency, i.e., low levels of circulating leptin. The invention also provides insight into the mechanisms by which leptin may regulate the pathology of NASH. The invention also provides insight into understanding the link between NASH and obesity, focusing on a potential mechanism that regulates fat deposition in the body. This mechanism involves the adipocyte hormone leptin which plays a key role in determining the status of energy availability and energy partitioning. Leptin has strong anti-steatotic effects proven in rodents and in rare human conditions such as in lipodystrophy syndromes.

SUMMARY OF THE INVENTION

The present invention relates the use of leptin polypeptides in the treatment of conditions associated with a fatty liver or elevated fat in the liver in a non-lipodystrophic subject. In one aspect, the subject has a relative leptin deficiency. Such methods generally would comprise administering an effective amount of a composition comprising a leptin polypeptide to the subject. In one aspect the subject is a mammal. In a further aspect, the mammal is human.

In another embodiment, the invention includes methods of treating nonalcoholic steatohepatitis (NASH) in a non-lipodystrophic subject. In a further embodiment, the invention includes methods of treating alcoholic fatty liver disease (AFLD) and/or nonalcoholic fatty liver disease (NAFLD) in a non-lipodystrophic subject.

In yet another embodiment, the invention includes methods of increasing mean serum leptin concentration in a non-lipodystrophic subject suffering from relative leptin deficiency comprising administering a composition comprising leptin in an amount effective to increase mean serum concentration in the subject.

The invention includes uses of leptin in decreasing fat content in the liver. The invention also provides leptin and uses thereof in the treatment of any condition associated with elevated fat content in the liver. Such conditions include, but are not limited to, alpha-1 anti-trypsin deficiency-induced fatty liver disease, parenteral nutrition induced fatty liver disease, simple steatosis associated with overweight and obesity, nonalcoholic and alcoholic steatohepatitis, and steatohepatitis associated with any form of hepatitis, including hepatitis C (HCV).

In one aspect, leptin decreases triglyceride accumulation in the liver. In another aspect, leptin ameliorates ballooning degeneration of the liver. Ballooning degeneration is evident by swelling of the hepatocytes and cytoplasmic vacuolation.

Uses of leptin compounds of the invention for the production of a medicament for the treatment or prevention of any condition or disease discussed herein are also provided. The leptin compounds of the invention are useful in the treatment or prophylaxis of those processes which involve fat deposition in the liver. Thus, uses of the compounds of the invention in the regulation of fat deposition and/or fat metabolism are provided. In one aspect, the compounds of the invention are useful in treating fatty liver disease. In another aspect, the compounds of the invention are useful in treating NASH.

In a further embodiment, the invention provides a method of treatment for a condition, described herein, wherein the composition includes the use of at least one additional factor. The additional factor, in various aspects, is selected from pramlinitide, peptide YY (PYY), exanatide, or analogues of any of these compounds. In another aspect, the additional factor is an insulin sensitizer including, but not limited to, a thiazolidinedione or metformin, or analogues of any of these compounds.

The invention further comprehends kits containing components for treating any fatty liver condition as set out above. Such a kit generally would comprise a composition comprising leptin polypeptide; and optionally, at least one additional factor selected from pramlinitide, peptide YY (PYY), exanatide, or an insulin sensitizer including, but not limited to, a thiazolidinedione or metformin, and analogues of any of these compounds.

The invention also includes the use of leptin in the production of a medicament for the treatment of a fatty liver condition in a non-lipodystrophic subject. In one aspect, the subject has a relative leptin deficiency.

In one embodiment, the fatty liver condition is nonalcoholic steatohepatitis (NASH), nonalcoholic fatty liver disease (NAFLD), or alcoholic fatty liver disease (AFLD). In another embodiment, the fatty liver condition is alpha-1 anti-trypsin deficiency-induced fatty liver disease, parenteral nutrition induced fatty liver disease, simple steatosis associated with overweight and obesity, nonalcoholic and alcoholic steatohepatitis, and steatohepatitis associated with any form of hepatitis, including hepatitis C (HCV). In a further embodiment, the fatty liver condition includes conditions ranging from ectopic lipid accumulation (steatosis) to cirrhosis In a further embodiment, the invention includes the use of leptin in the production of a medicament for increasing mean serum leptin concentration in a non-lipodystrophic subject suffering from relative leptin deficiency. In one aspect, the serum leptin concentration in a subject increases. In a further aspect, mean serum leptin concentration increases from approximately 6 ng/mL to approximately greater than 60 ng/mL after six months. In another aspect, mean serum leptin concentration increases from approximately 6 ng/mL to approximately 30 ng/mL after leptin treatment. In a various aspect, mean serum leptin concentration increased from approximately 6 ng/mL to approximately 15 ng/mL within the first month of leptin treatment. The invention includes an increase in mean serum leptin concentration to approximately 10 ng/mL, to approximately 20 ng/mL, to approximately 25 ng/mL, to approximately 30 ng/mL, to approximately 35 ng/mL, to approximately 40 ng/mL, to approximately 45 ng/mL, to approximately 50 ng/mL, to approximately 55 ng/mL, to approximately 60 ng/mL, to approximately 65 ng/mL, to approximately 70 ng/mL, to approximately 75 ng/mL, to approximately 80 ng/mL, to approximately 85 ng/mL, to approximately 90 ng/mL, to approximately 95 ng/mL, to approximately 100 ng/mL, to approximately 150 ng/mL, and to approximately 200 ng/mL.

The invention also includes the use of leptin in the production of a medicament for improving hepatitic steatosis in a non-lipodystrophic subject suffering from hepatitic steatosis. Such uses of leptin according to the invention decrease liver fibrosis or scarring, decrease liver inflammation, and decrease liver fat in the subject.

In another embodiment, the invention includes the use of leptin in the production of a medicament for improving liver function in a non-lipodystrophic subject suffering from decreased liver function. Such improvement in liver function is measured by improvements in liver function tests. Such use increases serum aspartate aminotransferase (AST) and decreases serum alanine aminotransferase (ALT). In various aspects, such uses of leptin improve, i.e. decrease the NASH score and decrease fasting serum triglyceride level. In further aspects, such uses of leptin improve insulin sensitivity or increase hepatic insulin sensitivity.

In another embodiment, the invention includes the use of leptin in the production of a medicament for increasing metabolic rate in a non-lipodystrophic subject. Such improvement in metabolic rate is measured by an increase in resting energy expenditure (REE) in the subject and/or an increase in the ratio of REE to lean body mass in the subject. Such improvement in metabolic rate is also measured by a decrease in respiratory quotient (RQ) in the subject.

In yet another embodiment, the invention includes the use of leptin in the production of a medicament for modulating messenger RNA or protein expression of genes associated with lipogenesis and lipid oxidation in a non-lipodystrophic subject. Such genes include, but are not limited to, glucokinase, peroxisomal proliferator activated receptor α, peroxisomal proliferator activated receptor γ, PPARγ coactivator 1, pyruvate kinase, sterol regulatory element binding protein-1c, long chain and very long chain acyl-CoA dehydrogenase or stearoyl-CoA desaturase, phosphoenoyl pyruvate kinase, microsomal transfer protein, arylacetaminde deacetylase, apolipoprotein C2, carnitine palmitoyl transferase II, and phospholipase D1.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations specifically mentioned above. With respect to aspects of the invention described as a genus, all individual species are individually considered separate aspects of the invention. Additional features and variations of the invention will be apparent to those skilled in

BRIEF DESCRIPTION OF THE DRAWINGS

FIG. 3 depicts the expression of candidate genes in human liver from normal control subjects and subjects with NAFLD. Panel A compares controls with all NAFLD subjects; whereas panel B compares controls with NAFLD and a BMI<30. Messenger RNA levels were quantified by qRT-PCR as described in the text.

FIG. 14A shows the top 10 cannonical pathways identified by Ingenuity Pathway Analysis of mRNA profiles of the liver biopsies.

DETAILED DESCRIPTION OF THE INVENTION

Figure 1:
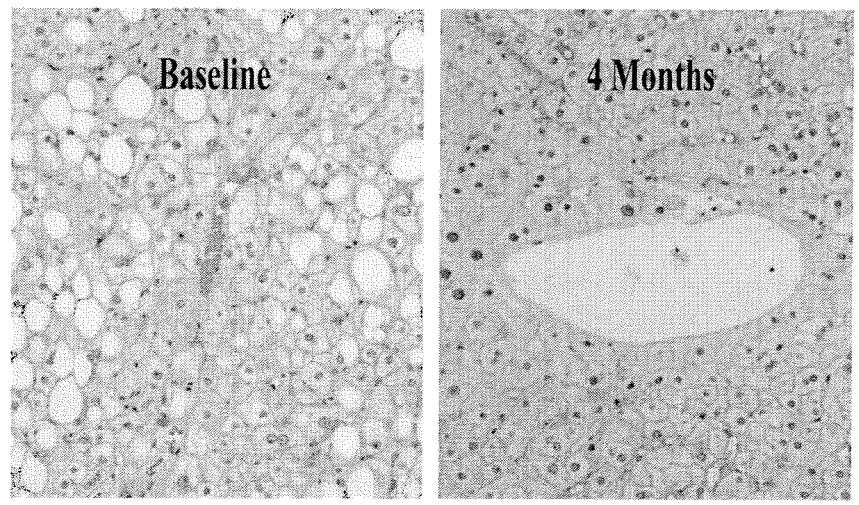
FIG. 1 shows the effect of recombinant leptin therapy on liver histology in lipodystrophic subjects, which formed a basis for examining the effect of leptin in fatty liver conditions in non-lipodystrophic subjects described herein. The significant triglyceride accumulation and ballooning degeneration was almost completely ameliorated by four months of leptin therapy.

Unprocessed human leptin is synthesized in vivo, for example, as a 167 amino acid, 16 kDa protein prohormone, which includes as N-terminal 21-amino acid signal sequence that is cleaved from the remainder of the polypeptide in order to generate a mature, circulating, 146 amino acid polypeptide hormone, which plays a key role in regulating energy intake and energy expenditure, including appetite and metabolism. Leptin is one of the most important adipose-derived hormones. The terms "leptin" "leptins" and "leptin polypeptide" as used herein encompass: naturally occurring human, mouse, rat, and other heterologous species leptins, and also includes recombinantly produced mature leptin, such as metreleptin (i.e., r-metHuLeptin), which is a 147 amino acid leptin analog generated by the genetically engineered N-terminal addition of a methionine to the N-terminal amino acid of the 146-amino acid, mature, circulating, human leptin; and biologically active fragments, agonist, analogs, agonist analogs, variants, fusion proteins, and other derivatives thereof, as available and that become available in the art (see, e.g., International Patent Publication Nos. WO 96/05309, WO 96/40912; WO 97/06816, WO 00/20872, WO 97/18833, WO 97/38014, WO 98/08512, WO 98/28427, WO 98/46257, WO 00/09165, WO 00/47741, and WO 00/21574; International Patent Applicant Nos. PCT/US96/22308 and PCT/US96/01471; U.S. Pat. Nos. 5,521,283, 5,532,336, 5,552,524, 5,552,523, 5,552,522, 5,935,810, 6,001,968, 6,429,290, 6,350,730, 6,936,439, 6,420,339, 6,541,033, 7,112,659, 7,183,254, and 7,208,577, U.S. Pat. Publication Nos. 2005/0176107, 2005/0163799; each of which is hereby incorporated by reference in its entirety and for all purposes. Leptin is the polypeptide product, for example, of the ob gene as described in the International Patent Publication No. WO 96/05309, and the U.S. patent application Ser. No. 08/483,211, each of which is incorporated herein by reference in its entirety. Also encompassed herein are all forms of leptin.

In one aspect, the invention includes r-metHuLeptin (A-100) or METRELEPTIN (SEQ ID NO: 1):

```
M V P I Q K V Q D D T K T L I K T I V T R I N D I
S H T Q S V S S K Q K V T G L D F I P G L H P I L
T L S K M D Q T L A V Y Q Q I L T S M P S R N V I
Q I S N D L E N L R D L L H V L A F S K S C H L P
W A S G L E T L D S L G G V L E A S G Y S T E V V
A L S R L Q G S L Q D M L W Q L D L S P G C
```

(Amylin Pharmaceuticals, Inc., San Diego, Calif.). Injectable recombinant leptin (A-100) has been given to about 15 children and adults with congenital leptin deficiency and to approximately 40 patients with various forms of lipodystrophy for periods ranging from a few months to three years. Phase I and II trials have been conducted for developing leptin as a therapy for obesity on hundreds of patients with short-term therapy. While the efficacy for weight loss in humans for treatment of all types of obesity is controversial, trials have shown that leptin therapy has not led to significant side effects apart from injection site reactions. In addition, initial studies reported herein in non-lipodystrophic patients have not shown any significant side effects of leptin therapy as discussed herein below.

In one aspect, the invention includes the treatment of patient with relative leptin deficiency (RLD). RLD, as discussed herein, indicates that a subject has lower than normal circulating levels of leptin for his or her age and gender. A subject might not have a deficiency in total body fat, but still might have leptin deficiency. Accepted criteria for RLD are shown in Table 1 herein.

Likewise, with the leptin studies conducted so far, there have been no consistent patterns of changes noted in hematological parameters, alanine aminotransferase (ALT), aspartate aminotransferase (AST), BUN, albumin and creatinphosphokinase (CPK) values. The development of antibodies to recombinant leptin was noted in 30% of subjects at higher dose levels (Investigator's Brochure), comparable to levels administered in the invention. The antibodies were non-neutralizing, and did not appear to be clinically significant (Investigator's Brochure). In one aspect of the invention, serum is saved from each patient at each visit to determine the levels of antibodies to leptin. Assays for determining leptin antibody concentration are available at Amgen Inc. (Thousand Oaks, Calif.).

Subjects are screened for occurrence of side effects at each visit. All adverse events occurring during studies of the invention, whether or not attributed to the study drug, are recorded and included in the investigator's annual investigational new drug (IND) report to the FDA. These adverse events include bruising, redness, pain, itching, inflammation, swelling, dark spots on skin, and lumps under the skin. Other frequently reported adverse events have been headache, fatigue, nausea and influenza-like symptoms. In one aspect, there may be additional risks such as potential allergic reaction to the study drug. There have been less frequent reports of generalized rashes, hives, and in rare instants, swelling of the lips and eyes. If the adverse event is sufficiently severe, the subject is removed from study and a termination assessment performed.

In one particular embodiment, the methods of the invention include the use of leptin to treat a fatty liver condition in a non-lipodystrophic subject. Lipodystrophy is a medical condition characterized by abnormal or degenerative conditions of the body's adipose tissue. In one aspect, lipodystrophy is a condition characterized by the absence of body fat. In a further aspect, patients with lipodystrophy demonstrate insulin resistance, dyslipidemia, and NASH. Thus, the term "non-lipodystrophic" as used herein excludes "lipodystrophic." Lipodystrophy is a medical condition characterized by abnormal or degenerative conditions of the body's adipose tissue. Thus, the invention includes the treatment of subjects that do not have "lipodystrophy" or are "non-lipodystrophic."

Fatty liver is also known as steatorrhoeic hepatosis or steatosis hepatitis. Fatty liver is a reversible condition where large vacuoles of triglyceride fat accumulate in liver cells via the process of steatosis. The term "condition" or "conditions" as used herein includes any disease, disorder, or physiological condition associated with fat in the liver.

Despite having multiple causes, fatty liver disease (FLD) can be considered a single disease that occurs worldwide in those with excessive alcohol intake (alcoholic fatty liver disease (AFLD)) and those who are obese (with or without effects of insulin resistance) (non-alcoholic fatty liver disease (NAFLD)). Fatty liver is also associated with other diseases that influence fat metabolism (Reddy et al., Am. J. Physiol. Gastrointest. Liver Physiol. 290:G852-G858, 2006). Morphologically it is difficult to distinguish alcoholic FLD (AFLD) from non-alcoholic FLD (NAFLD) and both show micro-vesicular and macrovesicular fatty changes at different stages. In one embodiment, the methods of the invention include the use of leptin to treat or provide therapeutic benefits for any fatty liver disease.

In addition, 10 to 20 percent of Americans suffer from a "fatty liver" in which there is no inflammation or liver damage, but there is fat in the liver. (NIH Publication No. 07-4921, supra). Although having fat in the liver is not normal, by itself it probably causes little harm or permanent damage. If fat is suspected based on blood test results or scans of the liver, this problem is called nonalcoholic fatty liver disease (NAFLD). If a liver biopsy is performed in this case, it will show that some people have NASH while others have simple fatty liver. The invention includes methods of treating NAFLD and AFLD with a composition comprising leptin.

In another embodiment, the invention includes methods of treating nonalcoholic steatohepatitis (NASH) in non-lipodystrophic subjects. NASH is a common, but all too often silent, liver disease. It resembles alcoholic liver disease, but occurs in people who drink little or no alcohol and it affects two to five percent of Americans (National Institutes of Health (NIH) Publication No. 07-4921, November 2006). The major feature in NASH is fat in the liver, along with inflammation and damage. Most people with NASH feel well and are not aware that they have a liver problem. Nevertheless, NASH can be severe and can lead to cirrhosis, in which the liver is permanently damaged and scarred and no longer able to work properly.

Both NASH and NAFLD are becoming more common, possibly because of an increasing occurrence of obesity in the general population. (NIH Publication No. 07-4921, supra). Obesity also contributes to diabetes and high blood cholesterol, which can further complicate the health of someone with NASH. Diabetes and high blood cholesterol are also becoming more common among Americans.

NASH is usually first suspected in a person who is found to have elevations in liver tests that are included in routine blood test panels, such as alanine aminotransferase (ALT) or aspartate aminotransferase (AST) (NIH Publication No. 07-4921, supra). When further evaluation shows no apparent reason for liver disease (such as medications, viral hepatitis, or excessive use of alcohol) and when x-rays or imaging studies of the liver show fat, NASH is suspected. The only means of proving a diagnosis of NASH and separating it from simple fatty liver disease is a liver biopsy. For a liver biopsy, a needle is inserted through the skin to remove a small piece of the liver. NASH is diagnosed when examination of the tissue with a microscope shows fat along with inflammation and damage to liver cells. If the tissue shows fat without inflammation and damage, simple fatty liver or NAFLD is diagnosed. An important piece of information learned from the biopsy is whether scar tissue has developed in the liver. Currently, no blood tests or scans can reliably provide this information.

NASH is usually a silent disease with few or no symptoms. Patients generally feel well in the early stages and only begin to have symptoms, such as fatigue, weight loss, and weakness once the disease is more advanced or cirrhosis develops (NIH Publication No. 07-4921, supra). The progression of NASH can take years, even decades. The process can stop and, in some cases, reverse on its own without specific therapy. On the other hand, NASH can slowly worsen, causing scarring or "fibrosis" to appear and accumulate in the liver. As fibrosis worsens, cirrhosis develops; the liver becomes seriously scarred, hardened, and unable to function normally (NIH Publication No. 07-4921, supra). Not every person with NASH develops cirrhosis, but once serious scarring or cirrhosis is present, few treatments can halt the progression. A person with cirrhosis experiences fluid retention, muscle wasting, bleeding from the intestines, and liver failure. Liver transplantation is the only treatment for advanced cirrhosis with liver failure, and transplantation is increasingly performed in people with NASH. NASH ranks as one of the major causes of cirrhosis in America, behind hepatitis C and alcoholic liver disease. Thus, the invention provides methods for the treatment of NASH with leptin.

In another embodiment, the invention includes methods of using leptin in the treatment of steatosis. Steatosis (also called fatty change, fatty degeneration or adipose degeneration) is the process describing the abnormal retention of lipids within a cell. Steatosis reflects an impairment of the normal processes of synthesis and elimination of triglyceride fat. Excess lipid accumulates in vesicles that displace the cytoplasm. When the vesicles are large enough to distort the nucleus, the condition is known as macrovesicular steatosis, otherwise the condition is known as microvesicular steatosis. While not always particularly detrimental to the cell in mild cases, large accumulations can disrupt cell constituents, and in severe cases the cell may even burst. In one aspect, the invention includes methods of treating hepatic steatosis.

In a further embodiment, the invention includes methods of improving liver function. The liver is a vital organ present in vertebrates and some other animals, and it has a wide range of functions. Some of the functions of the liver included detoxification, protein synthesis, and production of biochemicals necessary for digestion. Some additional functions of the liver include glycogen storage, decomposition of red blood cells, plasma protein synthesis, hormone production, and detoxification. The liver also produces bile, an alkaline compound which aids in digestion, via the emulsification of lipids. In certain aspects, the invention includes methods of improving these various liver functions.

The compositions of the invention are used to prevent or to treat any of a large number of diseases and conditions associated with leptin deficiency in a non-lipodystrophic subject. The therapeutic methods of the present invention include methods for the amelioration of disorders or treatment of disorders associated with leptin and/or a leptin deficiency. Likewise, therapeutic compositions are included in the invention. Such compositions may comprise a therapeutically effective amount of a leptin composition alone or in admixture with a pharmaceutically or physiologically acceptable formulation agent selected for suitability with the mode of administration. Pharmaceutical compositions may comprise a therapeutically effective amount of one or more leptin compositions in admixture with a pharmaceutically or physiologically acceptable formulation agent selected for suitability with the mode of administration.

As mentioned herein above, it is contemplated that methods of the present invention will use leptin polypeptide in the treatment of fatty liver disease. Leptin is useful alone, or in combination with other compounds, which act to reduce fat content in the liver and improve patient outcome. The present section provides a description of how leptin is therapeutically administered in the methods of the invention.

One of the therapeutic embodiments of the present invention is the provision, to a subject in need thereof, compositions comprising leptin polypeptide. Leptin polypeptide is generated in alternative aspects through recombinant means or by automated peptide synthesis. The leptin formulations for such a therapy are selected based on the route of administration and may include liposome and micelle formulations as well as classic pharmaceutical preparations.

The leptin proteins are formulated into appropriate preparation and administered to one or more sites within the subject in a therapeutically effective amount. By "effective amount" the invention refers to that amount of human leptin polypeptide that is sufficient to support an observable change in the level of one or more biological activities of leptin. The change may be an increased level of leptin activity. In one aspect, the change is a decrease in the fat content of the liver or an improvement of hepatitic steatotis or a decrease in liver fibrosis or a decrease in liver scarring or a decrease in liver inflammation, or improved liver function. Such improvement in liver function may be seen by an increase in serum aspartate aminotransferase (AST) or a decrease in serum alanine aminotransferase (ALT) or a decrease in NASH score or a decrease in fasting serum triglyceride level or an improvement in insulin sensitivity.

In another aspect, the beneficial effect of leptin on a subject's liver function is, in one aspect, seen by favorable changes in messenger RNA or protein expression of glucokinase, peroxisomal proliferator activated receptor α, peroxisomal proliferator activated receptor γ, PPARγ coactivator 1, pyruvate kinase, sterol regulatory element binding protein-1c, long chain and very long chain acyl-CoA dehydrogenase or stearoyl-CoA desaturase. In a further aspect, the beneficial effect of leptin on a subject's liver function is seen by an improvement in messenger RNA or protein expression of phosphoenoyl pyruvate kinase, microsomal transfer protein, arylacetaminde deacetylase, apolipoprotein C2, carnitine palmitoyl transferase II, or phospholipase D1.

Those of skill in the art will understand that the amounts of human leptin polypeptides administered for therapeutic use vary. In one aspect, the protein composition is substantially free of contaminating factors, contamination level of less than 0.02% (w/w). Human leptin compositions, suitable for injection into a patient, are prepared, for example, by reconstitution with a pharmacologically acceptable diluent of a lyophilized sample comprising purified human leptin and stabilizing salts. Administration of the leptin composition is alternatively systemic or local as discussed herein below in detail, and comprise administration of a therapeutically-effective amount of the human leptin protein composition.

In addition to therapies based solely on the delivery of the leptin composition, combination therapy is specifically contemplated. In the context of the invention, it is contemplated that the human leptin therapy is used similarly in conjunction with other agents commonly used for the treatment of a fatty liver disease.

To achieve the appropriate therapeutic outcome, using the methods and compositions of the present invention, one would generally provide a composition comprising human leptin and at least one other therapeutic agent (second therapeutic agent). In the invention, it is contemplated that the second therapeutic agent is selected from pramlinitide, peptide YY (PYY), exanatide, or an insulin sensitizer including, but not limited to, a thiazolidinedione or metformin, and analogues of any of these compounds.

The combination therapy compositions is provided in a combined amount effective to produce the desired therapeutic outcome in the treatment of a fatty liver disease, including NASH. This process involves contacting the cells with a leptin polypeptide and the second agent(s) or factor(s) at the same time. This is achieved by administering a single composition or pharmacological formulation that includes both agents, or by administering two distinct compositions or formulations, at the same time, wherein one composition includes the leptin polypeptide therapeutic composition and the other includes the second therapeutic agent.

Alternatively, the leptin polypeptide treatment precedes or follows the other agent treatment by intervals ranging from minutes to weeks. In embodiments where the second therapeutic agent and the leptin polypeptide are administered separately, one would generally ensure that a significant period of time did not expire between the times of each delivery, such that the second agent and the leptin polypeptide would still be able to exert an advantageously combined effect. In such instances, it is contemplated that one administers both modalities within about 12-24 hours of each other and, in one aspect, within about 6-12 hours of each other, with a delay time of only about 12 hours being most preferred. In some situations, it is desirable to extend the time period for treatment significantly, however, where several days (2, 3, 4, 5, 6 or 7) to several weeks (1, 2, 3, 4, 5, 6, 7 or 8) lapse between the respective administrations.

Systemic delivery of human leptin polypeptide expression constructs or proteins to patients is a very efficient method for delivering a therapeutically effective gene to counteract the immediate clinical manifestations of a disease. Alternatively, local delivery of the human leptin polypeptide and/or the second therapeutic agent is appropriate in certain circumstances.

The pharmaceutical composition in certain aspects contains formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen sulfite); buffers (such as borate, bicarbonate, Tris HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta cyclodextrin or hydroxypropyl beta cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (in one aspect, sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company , 1990).

In one aspect of the invention, leptin is supplied as a single-use only glass vial containing a lyophilized cake, prepared in a formulation buffer consisting of 10 mM glutamic acid, 2% glycine, 1% sucrose, and 0.01% polysorbate 20 to pH 4.25. Upon reconstitution with 2.2 ml of sterile water, the cake yields a 5 mg/ml concentration of leptin. Leptin is stored in a secure location under controlled conditions. Once the single-use vial has been reconstituted, the drug is administered immediately (no more than three hours after reconstitution). Before injection, study medication is allowed to reach room temperature (15 to 30° C.).

The invention further provides methods of administering the compositions of the invention to a mammal. In one aspect, the mammal is human. An effective amount of a composition to be employed therapeutically will depend, for example, upon the therapeutic context and objectives. One skilled in the art will appreciate that the appropriate dosage levels for treatment will thus vary depending, in part, upon the molecule delivered, the indication for which the composition is being used, the route of administration, and the size (body weight, body surface or organ size) and condition (the age and general health) of the patient. Accordingly, the clinician may titer the dosage and modify the route of administration to obtain the optimal therapeutic effect.

In one aspect, a regimen for delivering the composition to a mammal would include administration of from 0.001 mg/kg body weight to about 1000 mg/kg, from about 0.01 mg/kg to about 100 mg/kg, from about 0.1 mg/kg to about 100 mg/kg, about 1.0 mg/kg to about 50 mg/kg, or from about 1 mg/kg to about 20 mg/kg, given in daily doses or in equivalent doses at longer or shorter intervals, e.g., every other day, twice weekly, weekly, monthly, semi-annually, or even twice or three times daily. Alternatively, dosages are measured in international units (IU) ranging from about 0.001 IU/kg body weight to about 1000 IU/kg, from about 0.01 IU/kg to about 100 IU/kg, from about 0.1 IU/kg to about 100 IU/kg, from about 1 IU/kg to about 100 IU/kg, from about 1 IU/kg to about 50 IU/kg, or from about 1 IU/kg to about 20 IU/kg. Administration may be oral, intravenous, subcutaneous, intranasal, inhalation, transdermal, transmucosal, or by any other route discussed herein.

In a further aspect, leptin is administered by subcutaneous injection at the doses specified herein. However, leptin may be administered by any of the methods discussed herein and as known in the art. In a further aspect, injections at a single site have a maximum allowable volume of 2.0 ml. It is contemplated that leptin may be injected at multiple sites or at a greater dosage if a greater concentration of leptin is needed. In another aspect, leptin is administered at approximately the same time each day. However, alternative times for delivery are included in the invention.

The pharmaceutical compositions can also be selected for parenteral delivery. Alternatively, the compositions may be selected for inhalation or for delivery through the digestive tract, such as orally. The preparation of such pharmaceutically acceptable compositions is within the skill of the art.

In one embodiment, a pharmaceutical composition may be formulated for inhalation. For example, a leptin composition may be formulated as a dry powder for inhalation. Pharmaceutical composition inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins.

It is also contemplated that certain formulations may be administered orally. In one embodiment of the present invention, leptin compositions which are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre systemic degradation is minimized. Additional agents can be included to facilitate absorption of the composition. Diluents, flavorings, low melting point waxes, vegetable oils, lubricants, suspending agents, tablet disintegrating agents, and binders may also be employed.

Another leptin composition may involve an effective quantity of leptin in a mixture with non-toxic excipients which are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional leptin compositions will be evident to those skilled in the art, including formulations involving compositions in sustained or controlled delivery formulations. Techniques for formulating a variety of other sustained or controlled delivery means, such as liposome or micelle carriers, bioerodible microparticles or porous beads and depot injections, are also known to those skilled in the art.

The frequency of dosing will depend upon the pharmacokinetic parameters of the leptin composition in the formulation used. Typically, a clinician will administer the composition until a dosage is reached that achieves the desired effect. The composition may therefore be administered as a single dose, or as two or more doses (which may or may not contain the same amount of the desired molecule) over time, or as a continuous infusion via implantation device or catheter. Further refinement of the appropriate dosage is routinely made by those of ordinary skill in the art and is within the ambit of tasks routinely performed by them. Appropriate dosages may be ascertained through use of appropriate dose response data.

In addition to the routes of administration disclosed herein, compositions of the invention can be introduced for treatment into a mammal by any mode, such as but not limited to, intravenous, intraperitoneal, intracerebral (intraparenchymal), intracerebroventricular, intramuscular, intraocular, intraarterial, intraportal, intralesional routes, intraarticular, intratumor, cerebrospinal, intrarectal and colon, topical, subconjunctival, intrabladder, intravaginal, epidural, intracostal, intradermal, inhalation, transdermal, transserosal, intrabuccal, oral, intranasal, dissolution in the mouth or other body cavities, instillation to the airway, insufflation through the airway, injection into vessels, tumors, organ and the like, and injection or deposition into cavities in the body of a mammal.

Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed release bolus, or continuous administration.

In some cases, it may be desirable to use compositions in an ex vivo manner. In such instances, cells, tissues, or organs that have been removed from the patient are exposed to compositions after which the cells, tissues and/or organs are subsequently implanted back into the patient.

Administration of the compositions of the invention can be carried out using any of several standard methods including, for example, continuous infusion, bolus injection, intermittent infusion, inhalation, or combinations of these methods. For example, one mode of administration that can be used involves continuous intravenous infusion. In such an approach, the infusion dosage rate of the compositions of the invention can be, for example, 0.001-0.5 mg/kg body weight/hour, more preferably 0.01-0.2 mg/kg/hour, and most preferably 0.03-0.1 mg/kg/hour, with the drug being infused over the course of, for example, 1-100, 10-100, or about 12, 24, 48, 72, 84 or 96 hours. The infusion of the compositions of the invention can, if desired, be preceded by a bolus injection. Such a bolus injection is given at a dosage ranging from about 0.001 to about 10 mg/kg. Variations in the dose and in the time period of infusion of the compositions of the invention may occur and are also included in the invention.

A single bolus injection may be given by intravenous infusion through, for example, a central access line or a peripheral venous line, or by direct injection, using a syringe. Such administration may be desirable if a patient is only at short-term risk for exposure to endotoxin, and thus does not need prolonged persistence of the drug. For example, this mode of administration may be desirable in surgical patients, if appropriate, such as patients having cardiac surgery, e.g., coronary artery bypass graft surgery and/or valve replacement surgery. In these patients, a single bolus infusion of drug can be administered over a period of four hours prior to and/or during surgery. (Note that the amount of drug administered is based on the weight and condition of the patient and is determined by the skilled practitioner.) Shorter or longer time periods of administration can be used, as determined to be appropriate by one of skill in this art.

In cases in which longer-term delivery of a compound of the invention is desirable, intermittent administration can be carried out. In these methods, a loading dose is administered, followed by either (i) a second loading dose and a maintenance dose (or doses), or (ii) a maintenance dose or doses, without a second loading dose, as determined to be appropriate by one of skill in this art.

To achieve further delivery of the compound in a patient, a maintenance dose (or doses) of the compound can be administered, so that levels of the compound are maintained in the blood of a patient. Maintenance doses can be administered at levels that are less than the loading dose(s), for example, at a level that is about ⅙ of the loading dose. Specific amounts to be administered in maintenance doses can be determined by a medical professional, with the goal that the compound level is at least maintained. Maintenance doses can be administered, for example, for about 2 hours every 12 hours beginning at hour 24 and continuing at, for example, hours 36, 48, 60, 72, 84, 96, 108, and 120. Of course, maintenance doses can be stopped at any point during this time frame, as determined to be appropriate by a medical professional.

The infusion methods described above can be carried out using catheters (e.g., peripheral venous, central venous, or pulmonary artery catheters) and related products (e.g., infusion pumps and tubing) that are widely available in the art. One criterion that is important to consider in selecting a catheter and/or tubing to use in these methods is the impact of the material of these products (or coatings on these products) on the size of the drug.

Additional catheter-related products that can be used in the methods of the invention can be identified by determining whether the material of the products alters size of the compound, under conditions consistent with those that are used in drug administration. In addition, in the event that a patient already has a catheter in place that does not maintain optimal drug size, a catheter insert that is made of a compatible material (e.g., a polyamide polymer) or that includes a compatible coating can be used so that the drug solution does not contact the surface of the incompatible catheter. Such an insert, having an outside diameter that is small enough to enable it to be easily inserted into the existing catheter, while maintaining an inside diameter that is large enough to accommodate solution flow of the compound, is placed within the existing catheter and connected to tubing or a syringe through which the drug is delivered.

Appropriate frequency of administration can be determined by one of skill in the art and can be administered several times per day. The compositions of the invention may also be administered once each day or once every other day. In the case of acute administration, treatment is typically carried out for periods of hours or days, while chronic treatment can be carried out for weeks, months, or even years.

Both chronic and acute administration can employ standard pulmonary drug administration formulations, which can be made from the formulations described elsewhere herein. Administration by this route offers several advantages, for example, rapid onset of action by administering the drug to the desired site of action, at higher local concentrations. Pulmonary drug formulations are generally categorized as nebulized (see, e.g., Flament et al., Drug Development and Industrial Pharmacy 21(20):2263-2285, 1995) and aerosolized (Sciarra, "Aerosols," Chapter 92 in Remington's Pharmaceutical Sciences, 16th edition (ed. A. Osol), pp. 1614-1628; Malcolmson et al., *PSTT* 1(9):394-398, 1998, and Newman et al., "Development of New Inhalers for Aerosol Therapy," in Proceedings of the Second International Conference on the Pharmaceutical Aerosol, pp. 1-20) formulations.

EXAMPLES

The invention is described in more detail with reference to the following non-limiting examples, which are offered to more fully illustrate the invention, but are not to be construed as limiting the scope thereof. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention. All patents and publications mentioned herein are incorporated by reference.

Example 1

Leptin in Patients with Lipodystrophy

Characteristics of nonalcoholic-steatohepatitis (NASH) in patients with various forms of lipodystrophy were previously studied. Lipodystrophy is a medical condition characterized by abnormal or degenerative conditions of the body's adipose tissue, and patients with lipodystrophy demonstrate insulin resistance, dyslipidemia, and NASH.

Leptin levels in lipodystrophy and leptin's relationship to adiposity were studied (Oral et al., *N. Engl. J. Med.* 346:570-578, 2002). As with most individuals, circulating leptin levels correlated with total body adiposity in patients with various forms of lipodystrophy. However, a group of patients with levels less than the $5^{th}$ percentile of the general population were identified (Oral et al., supra), and patients with low levels of leptin were included in a trial of leptin replacement. To determine the metabolic effects of leptin administration in lipodystrophy, recombinant human leptin (Amgen Inc, Thousand Oaks, Calif.) was administered at doses to achieve high-normal levels of circulating leptin for four months in a group of eight diabetic subjects (Oral et al., supra). The group had poor metabolic control with a mean glycosylated hemoglobin (HbAlc) value of 9.1±0.5%. HbAlc is a molecule in red blood cells that attaches to glucose or blood sugar. Thus, glycosylated hemoglobin is indicative of amount of glucose in the blood. After four months of leptin replacement therapy, HbAlc decreased by a mean of 1.9 percentage points (95% CI, 1.1 to 2.7%, P=0.001) despite decreasing or discontinuing baseline anti-diabetic therapy (Oral et al., supra). At the end of four months of recombinant leptin therapy, fasting triglyceride levels fell by 60% (CI, 43 to 77%, p<0.001) and fasting free fatty acids fell from 1540±407 μmol/L to 790±164 μmol/L (P=0.05) (Oral et al., supra).

In the low-leptin (leptinemic), lipodystrophic patients described above, leptin treatment resulted in improved liver function tests (AST 66±16 U/L to 24±4 U/L; P=0.02 and ALT 53±12 U/L to 21±2 U/L; p=0.03) and an average of 28% decrease in liver volume (p=0.002). In a related study, it was found that this reduction in liver size is due to mobilization of intrahepatic triacylglycerol (Petersen et al., *J. Clin. Invest.* 109:1345-1350, 2002). Muscle triacylglycerol levels were also significantly decreased. The most striking effect of leptin therapy was a near-complete reversal of steatosis (FIG. 1). In addition, ballooning degeneration, accepted as an indication of oxidative stress (Brunt et al., *Am. J. Gastroenterol.* 94:2467-2474, 1999; Brunt, *Semin. Liver Dis.* 21:3-16, 2001), improved significantly (FIG. 1). All of the first 10 patients who had undergone a liver biopsy had met the histological definition of NASH at baseline. In eight of the 10 patients, the liver histopathology could not be classified as NASH after 4 months of therapy (Javor et al., *Hepatology* 41:753-760, 2005). While there were improvements in inflammation scores, the improvements did not reach statistical significance (Javor et al. supra). All in all, leptin administration in patients with lipodystrophy derived many beneficial effects from the leptin treatment.

Example 2

Studies in Non-Lipodystrophic Patients with NASH

Because leptin had a profound effect on the liver histopathology of NASH observed in low-leptin lipodystrophy, experiments were carried out to determine the effects of leptin on more commons form of NASH seen in the general population and in patients without lipodystrophy.

Clinical NASH is very heterogeneous in clinical characteristics, suggesting that there is heterogeneity in etiology as well. Therefore, if leptin has a biological role in modulating NASH pathology, even in a subgroup of patients with NASH, two observations should hold true: (1) NASH patients with differing degrees of leptinemia should have different clinical characteristics; and (2) NASH patients with low leptin levels should benefit (i.e., improved NASH score or improved liver pathology) from restoration of leptin levels to normal.

Figure 2:
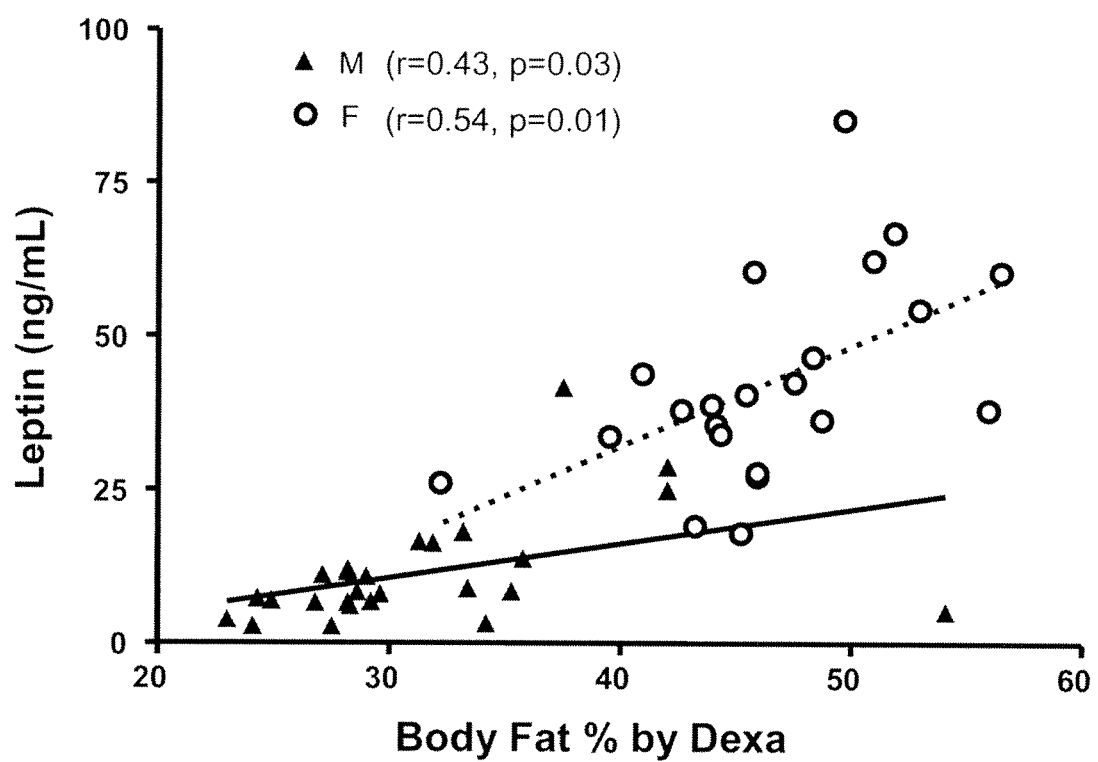
FIG. 2 shows serum leptin levels plotted against total body fat % determined via DEXA in 50 non-diabetic NASH patients. Values from male (M) and female (F) patients are shown distinctively.

In order to investigate the first hypothesis, serum leptin levels were measured in 50 non-diabetic, non-cirrhotic subjects with biopsy proven NASH (FIG. 2) who underwent fasting (minimum of 8 hours of fasting, 8 hours of sleep one night prior to blood sampling). The subjects' alcohol consumption was less than 40 grams/week and no subject had evidence of other etiologies of chronic liver disease. These patients were classified into three subgroups: (1) relative leptin-deficiency (RLD): patients with levels of leptin <$25^{th}$ percentile of NHANES III population based on their gender and body mass index; (2) normal leptin levels (NLL): patients with leptin levels falling between the $25^{th}$ and $75^{th}$ percentile of NHANESIII population based on gender and body mass index; and (3) relative-leptin excess (RLE): patients with leptin levels >$75^{th}$ percentile of NHANES III population based on gender and body mass index.

Table 1 shows the criteria for persons considered to have either a leptin deficiency or a leptin excess; the cut-offs for the $25^{th}$ and $75^{th}$ percentiles for the NHANES III population were provided by Dr. Constance E. Ruhl (Social & Scientific Systems, Inc.); partial data have been published (Ruhl et al., *Am. J. Clin. Nutr.* 74:295-301, 2001). It is important to note that the definition of relative leptin deficiency is somewhat arbitrary. The present studies are based on the hypothesis that that a leptin level less than one standard deviation of the population mean is indicative of biological significance. There is also an important clinical reason to choose this cut-off; retrospective analyses of pooled data available from leptin trials for obesity were suggestive that individuals with baseline leptin levels below the $25^{th}$ percentile had a greater degree of weight loss (based on personal communication, Dr. Alex DePaoli, Amgen Inc.).

TABLE 1

Accepted Criteria for Relative Leptin Deficiency and Excess

| Body Mass Index (BMI) (kg/m2) | Relative Leptin Deficiency (<$25^{th}$ percentile) (RLD) | | Relative Leptin Excess (<$75^{th}$ percentile) (RLE) | |
|---|---|---|---|---|
| | Females (ng/mL) | Males (ng/mL) | Females (ng/mL) | Males (ng/mL) |
| <25.0 | <5.0 | <2.0 | >12.1 | >4.9 |
| 25.0-27.5 | <12.0 | <3.2 | >20.2 | >7.2 |
| 27.5-30.0 | <14.0 | <4.0 | >25.3 | >9.6 |
| 30.0-35.0 | <18.0 | <7.0 | >31.5 | >14.6 |
| >35.0 | <25.7 | <10.9 | >43.0 | >21.6 |

Biochemical and morphological parameters in persons with relative leptin deficiency, normal leptin levels, and relative leptin excess were analyzed. Table 2 summarizes the data with differences between groups assessed using analysis of variance analysis (ANOVA) or chi-square where appropriate. As Table 2 demonstrates, patients with leptin deficiency are mostly male (10/11) with lower subcutaneous fat percentages. Their leptin level percentiles varied from 5 to 25, and the median percentile was 10. The leptin-deficient group had a comparable mean BMI with the other two groups. Also, patients in the leptin-deficient group demonstrated comparable (or even greater) amounts of visceral fat. The group with relative leptin excess demonstrated a trend toward a greater degree of insulinemia and a greater homeostatic model assessment (HOMA) value (HOMA is a method used to quantify insulin resistance and beta-cell function first described by Matthews et al., *Diabetologia* 28: 412-419, 1985), indicating worse insulin-resistance.

TABLE 2

Characteristics of Patients with NASH Stratified According to Their Leptin Levels

| Parameters | Relative Leptin Deficiency (RLD) | Normal Leptin Levels (NLL) | Relative Leptin Excess (RLE) | p-value |
|---|---|---|---|---|
| Number | 11 | 13 | 26 | N/A |
| Male/Female | 10/1 | 6/7 | 11/15 | 0.002 |
| Leptin (ng/mL) | 6.5 ± 4.3 | 23.4 ± 13.8 | 36.1 ± 22.4 | <0.001 |
| Fat by DEXA (%) | 32.2 ± 3.2 | 37.7 ± 9.4 | 42.4 ± 8.3 | 0.02 |
| BMI (kg/m$^2$) | 30.3 ± 3.2 | 31.0 ± 4.5 | 33.4 ± 8.4 | NS |
| Intra-abdominal fat volume by CT (cc.) | 211 ± 65 | 167 ± 71 | 201 ± 83 | 0.06 |
| Subcutaneous fat volume by CT (cc.) | 293 ± 120 | 403 ± 173 | 447 ± 178 | 0.02 |
| Fasting triglycerides (mg/dL) | 238 ± 290 | 153 ± 82 | 176 ± 98 | NS |
| Total cholesterol (mg/dL) | 186 ± 35 | 218 ± 54 | 213 ± 47 | 0.15 |
| Fasting insulin (uU/mL) | 11.9 ± 4.5 | 15.5 ± 7.3 | 11.2 ± 4.6 | 0.11 |
| HOMA | 2.9 ± 1.3 | 4.0 ± 1.8 | 4.6 ± 3.0 | 0.09 |
| Free fatty acids (mEq/L) | 498 ± 170 | 357 ± 135 | 451 ± 202 | 0.18 |
| Adiponectin (ug/mL) | 5.5 ± 3.2 | 5.3 ± 4.0 | 8.7 ± 3.2 | 0.03 |
| NASH ACTIVITY SCORE | 3.1 ± 2.0 | 3.3 ± 1.7 | 3.7 ± 1.9 | NS |
| STEATOHEPATITIS SCORE | 1.6 ± 0.5 | 1.4 ± 0.6 | 1.5 ± 0.6 | NS |

Because the overwhelming majority of patients in the RLD group were male, further analyses in these patients only were carried out to see if the differences in various parameters were related to differences in sex distribution observed between the three groups. These results are presented in Table 3. The data indicate that the general trends described above still hold true in the male patients. The male RLD group still showed higher visceral adiposity. Interestingly, when males were taken alone, the inter-group differences noted in free fatty acid (FFA) levels achieve a higher level of significance compared to the analyses involving both male and female patients. In addition, these patients demonstrated greater steatohepatitis scores. Thus, NASH patients, when stratified according to their leptin levels, display differences in body composition and interesting metabolic as well as histopathological features.

system (Qiagen). PCR amplification was carried out for 40 cycles and gene expression was determined from the inflection point of the tracing (Ct). All samples had Ct values <35. All data was normalized to 18S mRNA levels determined in each sample. Preliminary experiments showed that the levels of 18S were linear over a 1000-fold dilution of the cDNA and the samples were routinely diluted 1:100 for assay. The levels of target RNA determined by quantitative PCR (qPCR) varied <8% with different input RNA amounts. The data represents quantification of duplicate cDNA preparations, run in duplicate in two independent RT and PCR reactions. Data was normalized such that the level of mRNA from the control samples was =1.

As shown in FIG. 3, the results from the subjects with a BMI<30 kg/m$^2$ were not significantly different than the whole cohort. The expression levels of mRNAs encoding

TABLE 3

Characteristics of Male Patients with NASH Stratified According to Their Leptin Levels

| Parameters | Relative Leptin Deficiency (RLD) | Normal Leptin Levels (NLL) | Relative Leptin Excess (RLE) | p-value |
|---|---|---|---|---|
| Number | 10 | 6 | 11 | N/A |
| Leptin (ng/mL) | 5.3 ± 2.0 | 11.1 ± 3.6 | 16.8 ± 10.9 | 0.006 |
| Fat by DEXA (%) | 29.0 ± 4.3 | 31.3 ± 9.4 | 35.8 ± 5.4 | 0.09 |
| BMI (kg/m$^2$) | 30.7 ± 3.4 | 30.4 ± 3.7 | 29.8 ± 3.8 | NS |
| Intra-abdominal fat volume by CT (cc.) | 218 ± 89 | 164 ± 75 | 179 ± 75 | 0.15 |
| Subcutaneous fat volume by CT (cc.) | 288 ± 128 | 333 ± 87 | 343 ± 108 | 0.26 |
| Fasting triglycerides (mg/dL) | 256 ± 182 | 196 ± 103 | 214 ± 110 | NS |
| Total cholesterol (mg/dL) | 179 ± 29 | 193 ± 31 | 211 ± 44 | 0.15 |
| Fasting insulin (uU/mL) | 11.6 ± 4.6 | 17.3 ± 7.0 | 21.5 ± 14.7 | 0.11 |
| HOMA | 2.7 ± 1.4 | 4.1 ± 1.8 | 5.2 ± 3.8 | 0.12 |
| Free fatty acids (mEq/L) | 496 ± 181 | 313 ± 105 | 357 ± 160 | 0.05 |
| Adiponectin (ug/mL) | 5.5 ± 3.4 | 3.3 ± 1.7 | 6.7 ± 3.6 | 0.05 |
| NASH ACTIVITY SCORE | 2.9 ± 2.1 | 2.8 ± 1.0 | 3.3 ± 1.7 | NS |
| STEATOHEPATITIS SCORE | 1.6 ± 0.5 | 1.0 ± 0.1 | 1.3 ± 0.7 | 0.10 |

Experiments were also carried out to determine whether the human liver in patients with hepatic steatosis responds with altered gene expression in a similar manner to that seen in rodent models of hepatic steatosis. Samples were obtained from ten "control" individuals during open liver resection for non-neoplastic disease. These ten controls were non diabetic and the samples were histologically normal without evidence of steatosis. The mean age was 60.0±11.1 years and mean BMI was 26.4±2.6 kg/m$^2$.

Expression of mRNA was also determined in a group of subjects with biopsy-proven non-alcoholic fatty liver disease (NAFLD) (n=33; mean age was 49±12.4 years; mean BMI was 31.1±5.0 kg/m$^2$). A subgroup of these subjects who were non-obese and who had NAFLD were also examined (n=14; mean age was 46.1±11.0 years; mean BMI was 26.1±3.1 kg/m$^2$).

To assess expression of individual genes, a two microgram (μg) aliquot of total RNA was reverse-transcribed using random hexamers to generate single-strand cDNA using MMLV Reverse Transcriptase according to the manufacturers protocol (Promega). Real-time PCR was carried out using an Opticon Cycler (MJ Research) using conditions specific for each primer set. Two microliters of cDNA was amplified in a final volume of 25 μL using the Qiagen CyberGreen Quantitec peroxisome proliferator-activated receptorγ1 (PPARγ1) (not shown), CCAAT/enhancer binding protein δ (C/EBPδ) (not shown), PPARα, PPARγ2, sterol regulatory element binding protein 1 (SREBP-1), and stearoyl-coenzyme A desaturase 1 (SCD-1) were elevated when compared to controls (FIG. 3). Identical results were seen in animal models of hepatic steatosis (Reddy et al., *Annu. Rev. Nutr.* 21:193-230, 2001; Shimomura et al., *J. Biol. Chem.* 274:30028-30032, 1999; and Chao et al., *J. Clin. Invest.* 106:1221-1228, 2000). No difference was found in the mRNA expression of phosphoenolpyruvate carboxykinase (PEPCK) compared to control, likely because the subjects were fasting and non-diabetic. There was a significant increase in the levels of the mitochondrial oxidative genes, Long Chain Acyl CoA Dehydrogenase (LCAD) and Very Long Chain Acyl CoA Dehydrogenase (VLCAD), which are PPARα-regulated and were shown to have increased in a high fat feeding experiment in mice (de Fourmestraux et al., *J. Biol. Chem.* 279:50743-50753, 2004). Interestingly, there was a down-regulation of genes associated with very low density lipoprotein (VLDL) assembly, including microsomal triglyceride transfer protein (MTP). Decreases in MTP activity are found in people with fatty liver disease associated with type 2 diabetes (Bernard et al., *Diabetologia* 43:995-999, 2000). In addition, previous studies have shown that the inhibition of hepatic VLDL secretion is one of the major causes of fatty liver disease (Day et al., Biochim. Biophys. Acta. 1215:33-48, 1994; Grunnet et al., Biochem. J. 228:673-681, 1985; Venkatesan et al., Biochim. Biophys. Acta. 960:61-66, 1988) and that MTP is crucial to VLDL secretion (Atzel et al., Biochemistry 32:10444-10450, 1993; Benoist et al., Eur. J. Biochem. 240:713-720, 1996).

Thus, research has shown that patients with severe leptin deficiency due to lipodystrophy have significant metabolic abnormalities and liver pathology which can be reversed with exogenous leptin therapy. A significant subset of patients with NASH appear to have relatively low leptin levels. These subjects have a relative decrease in subcutaneous fat with an increase in visceral fat, which may explain the relative leptin deficiency. Further, it is believed that this phenotypic difference is very important. Given the remarkable response of lipodystrophic patients to leptin, a trial of leptin therapy in individuals with NASH is appropriate for individuals with relatively low leptin levels who do not have clinical lipodystrophy.

These experiments have also demonstrated changes in liver gene expression in humans with NAFLD, which parallel the changes in liver gene expression seen in animal models of hepatic steatosis. These studies also demonstrated that tools are available to determine the effects of leptin in patients with different forms of NASH. Moreover, these studies have shown that the expression of mRNA and protein levels of key genes related to lipid and carbohydrate metabolism in human liver biopsy samples can be examined and can provide useful information. For example, SCD-1, a gene which appears to be strongly modulated by leptin action in rodents, is up-regulated in NAFLD, suggesting that leptin therapy may have a potential effect. Preliminary studies demonstrate that the patient population is available and the techniques are in hand to carry out the following studies.

Example 3

Recombinant Leptin Therapy Reduces Fat Content in the Liver in Subjects with NASH and Relative Leptin Deficiency Recombinant leptin therapy improves insulin sensitivity and dyslipidemia and reverses nonalcoholic steatohepatitis (NASH) in leptin-deficient lipodystrophy in humans. Based on these prior observations, a study was carried out to determine if recombinant leptin therapy would be effective in reversing the histopathological changes as well as fat deposition in patients with biopsy proven NASH (NASH activity score 3 or greater with a minimum score of 1 on steatosis, inflammation and hepatocellular injury and/or fibrosis) and relative leptin deficiency (circulating leptin levels <25th percentile of BMI matched controls from NHANES III population).

In a pilot efficacy trial, nine non-diabetic men [age: 32 to 53 years, weight: 77.9 to 106.2 kgs, BMI: 26.2 to 31.8 kg/m$^2$, circulating leptin levels: 2.7 to 8.1 ng/dL, NASH activity score: 3 to 11 (based upon histopathological evaluation according to the method of Kleiner et al. (Hepatology 41:1313-1321, 2005), ALT: 26 to 257 IU/L] were enrolled in a one year study. Seven of the nine men were put on lipid lowering therapy with a statin or a fibrate for dyslipidemia; one of the nine men was put on metformin for impaired glucose tolerance (IGT); and two of the nine were put on antidepressive medications. These nine men with intact hepatic synthetic function were enrolled in the study where no dosing changes are allowed in the cited drugs during the one year study period. The first four of these subjects have completed six months of recombinant leptin therapy (METRELEPTIN, Amylin Pharmaceuticals, Inc., San Diego, Calif.) given subcutaneously daily at a dose of 0.1 mg/kg/day.

As shown in Table 4, after six months of leptin treatment, body weight and liver fat, as measured by MRI and MR spectroscopy (MRS), decreased in three of the four subjects. All subjects underwent a liver biopsy at baseline and are expected to undergo another liver biopsy at 12 months of the study.

TABLE 4

Preliminary Findings in Four Subjects

| Subject | Weight Baseline (kg) | Weight After 6-mo. (kg) | Liver Fat Baseline (%) | Liver Fat After 6-months (%) |
|---|---|---|---|---|
| NASH-1 | 82.3 | 76.0 | 9 ± 3 by MRI<br>15 by MRS | 7 ± 3 by MRI<br>9 by MRS |
| NASH-2 | 83.8 | 78.7 | 16 ± 4 by MRI<br>16 by MRS | 8 ± 2 by MRI<br>4 by MRS |
| NASH-3 | 106.2 | 106.8 | 32 ± 3 by MRI<br>29 by MRS | 31 ± 3 by MRI<br>32 by MRS |
| NASH-4 | 89.0 | 86.9 | 22 ± 3 by MRI<br>25 by MRS | 17 ± 3 by MRI<br>10 by MRS |

Overall, recombinant leptin therapy was well-tolerated: 2/9 subjects experienced transient injection site reactions (starting around three weeks and subsiding within four weeks). These results indicate that a subset of patients with NASH, with lower leptin levels at baseline, benefit from leptin therapy in that they have shown weight reduction as well as a decrease, i.e. improvement, in hepatic fat content.

Example 4

Recombinant Leptin Therapy in Subjects with NASH and Relative Leptin Deficiency

Recombinant leptin therapy is carried out on a greater patient population. For inclusion in the study, patients must meet the following criteria: adult male patients age>18 years and <65 years; BMI<40 kg/m$^2$; abnormal liver enzymes and/or fatty liver change on imaging; alcohol consumption of less than 40 grams/week; no evidence of other etiologies of chronic liver disease (viral hepatitis, autoimmune liver disease); a liver biopsy meeting the histopathological definition of NASH; and demonstration of a relative leptin deficiency (RLD) based on the criteria indicated in Table 1. Nonalcoholic fatty liver disease appears to be more common among Hispanics, Native Americans, and African Americans according to the NHANES study using pre-defined clinical criteria. In this study, all patients with biopsy-proven NASH, regardless of race and ethnicity, are included.

Women are excluded from the initial study because the rate of RLD is significantly lower in women patients compared to male patients. In preliminary experiments, 12 of 84 patients had met the criterion for RLD and only one was a woman. Future studies are designed to include women with RLD.

Patients are excluded from the study if they demonstrate any of the following criteria: the presence of advanced liver disease (as evidenced by abnormal synthetic function, abnormal prothrombin time (PT) or albumin); the presence of clinical lipodystrophy; the presence of other liver disease; the presence of clinical diabetes (fasting >126 mg/dL or 2 hour post 75 g-glucose >200 mg/dL or random glucose>200 mg/dL with presence of diabetes symptoms or known history of diabetes); are currently on medication for the treatment of NASH or obesity; the presence of HIV; the inability to give informed consent; the presence of end stage renal disease (ESRD); any type of active cancer, or >class 2 congestive heart failure; the presence of any other condition that limits life expectancy to <2 years, the presence of active infection (may be transient); or any other condition in the opinion of the investigators that may impede successful data collection.

An outpatient visit consists of a full history and physical exam, and a standard oral glucose tolerance test (administration of 75 gram of dextrose after an overnight fast). The baseline and two hour glucose levels are determined. BMI is calculated as weight (kg)/height (m$^2$). Fasting leptin measurements are obtained to confirm the original level. Subjects with values that fall outside of the originally documented relative leptin deficiency are excluded from the study.

The goal is to determine the efficacy of recombinant leptin therapy on liver histopathology and metabolic characteristics of patients with NASH who have relative leptin deficiency at baseline. The study focuses on the efficacy of restorative leptin therapy on the amelioration of pathological features of NASH. In addition, the study evaluates the impact of leptin therapy on total body insulin sensitivity and lipid levels.

Leptin is supplied as a single-use only glass vial containing a lyophilized cake, prepared in a formulation buffer consisting of 10 mM glutamic acid, 2% glycine, 1% sucrose, and 0.01% polysorbate 20 to pH 4.25. Upon reconstitution with 2.2 ml of sterile water, the cake will yield a 5 mg/ml concentration of leptin.

Leptin (recombinant methionyl-human leptin) is provided by Amylin Pharmaceuticals, Inc. (San Diego, Calif.) and is administered subcutaneously at the same time each day to achieve high normal levels of circulating leptin in individuals who started out with lower than normal or low normal levels of circulating leptin. 43,73 Previous experience from patients with lipodystrophy or with congenital absence of leptin indicate that this goal can be achieved by administration of 0.02 to 0.10 mg/kg/day in adult males, depending on baseline leptin concentrations and body surface area of the patients. In this study, patients are treated with 0.1 mg/kg/day of leptin to achieve high physiological concentrations of leptin. (This dosage is anticipated to achieve leptin levels from a mean of 6 ng/mL to a mean of 15 ng/mL after only one month of leptin treatment). It is contemplated that this dosage of leptin can further increase a subject's serum level of leptin over time. For example, it is contemplated that serum leptin may increase from about 1 ng/mL to about 2 ng/mL to about 3 ng/mL to about 4 ng/mL to about 5 ng/mL to about 6 ng/mL to about 7 ng/mL to about 8 ng/mL to about 9 ng/mL to about 10 ng/mL to about 15 ng/mL to about 20 ng/mL to about 25 ng/mL to about 30 ng/mL to about 40 ng/mL to about 50 ng/mL to about 60 ng/mL to about 70 ng/mL to about 80 ng/mL to about 90 ng/mL to about 100 ng/mL to about 200 ng/mL. The greater dose is selected taking into account the relatively greater body surface area and greater baseline leptin levels compared to patients with lipodystrophy. In these patients, the dose and concentration curve is anticipated to be shifted to the right. Patients are treated at 0.1 mg/kg/day until the end of one year.

At the end of four weeks, subjects have liver function tests, and blood work (CK and CBC) drawn for assessing safety. If subjects tolerate the injections without any problems, they are periodically (3 months, 6 months, 9 months and 1 year) evaluated and get monthly lab tests as described above. The dosage remains at 0.1 mg/kg/day dose until the treatment period is completed at 12 months.

After four months of leptin treatment, there has been a mean improvement of 3 points in the global NASH scores (as determined by the method of Kleiner et al., supra) of patients. At least this much improvement (for example, 3 points in 12 months) has been determined to be a clinical improvement. With a difference in mean NASH score of 2 (before and after leptin treatment) with an SD of 1; 95% power and 5% of significance level, it has been determined that at least eight patients are needed for this study using paired t-test analysis. Assuming a possible 20% dropout rate, the study requires at least 10 patients with relative leptin deficiency for treatment with recombinant leptin for a period of 12 months. A twelve month time period for the study was chosen in order to allow for fibrosis scores to change. Previously, in the lipodystrophy trial, there was not as much improvement in fibrosis scores after only four months of therapy. Studies with the thiazolidinediones after 48 weeks of therapy have demonstrated improvement in both global NASH scores as well as fibrosis scores.

A detailed evaluation of patients is carried out at baseline (prior to treatment) and at one year. Patients are also evaluated at the end of the sixth week, and then after the third, sixth, and ninth months as outpatients. Leptin tolerability is assessed at each visit. During each visit, height, weight, BMI, injection site inspection, and basic laboratory data (levels of fasting insulin, fasting triglyceride, fasting leptin, electrolytes, BUN, creatinine, calcium, ALT, AST, gamma-glutamyl transpeptidase (GGT), bilirubin, and alkaline phosphatase) are recorded. Throughout the study, lab work for complete blood count (CBC), liver function tests, and creatinine kinase are obtained monthly. At the end of the year, patients undergo another liver biopsy and the specimen is graded for the severity of NASH pathology. Table 5 summarizes the tests and therapy modifications to be carried out at each visit.

TABLE 5

Tests and Therapy Modifications During the Study

| Tests/<br>Therapy<br>Modifications | Baseline* | 6 weeks | 3 months | 6 months | 9 months | 12 months | 15 months | 18 months |
|---|---|---|---|---|---|---|---|---|
| Fasting biochemistry | YES | YES | YES | YES | YES | YES | YES | YES |
| Fasting adipocytokines | YES | YES | YES | YES | YES | YES | YES | YES |
| Fasting appetite regulators | YES | YES | YES | YES | YES | YES | YES | YES |
| Leptin sampling | YES | YES | YES | YES | YES | YES | YES | YES |
| REE | YES | YES | YES | YES | YES | YES | YES | YES |

TABLE 5-continued

Tests and Therapy Modifications During the Study

| Tests/<br>Therapy<br>Modifications | Baseline* | 6 weeks | 3 months | 6 months | 9 months | 12 months | 15 months | 18 months |
| --- | --- | --- | --- | --- | --- | --- | --- | --- |
| IVGTT | YES | NO | NO | NO | NO | YES | YES | YES |
| Anthropometry | YES | YES | YES | YES | YES | YES | YES | YES |
| DEXA | YES | NO | NO | NO | NO | YES | YES | YES |
| MRI | YES | NO | NO | NO | NO | YES | YES | YES |
| Liver biopsy | Recent | NO | NO | NO | NO | YES | NO | NO |
| Leptin therapy | 0.1 mg/kg/day | 0.1 mg/kg/day | 0.1 mg/kg/day | 0.1 mg/kg/day | 0.1 mg/kg/day | 0.1 mg/kg/day | Diet modified | Diet ad lib |

Differences in each collected parameter are statistically evaluated using a paired t-test. If data are skewed, such as in triglyceride levels, nonparametric tests are used. A P<0.05 is considered significant. If a significant difference is demonstrated between baseline and after one year of treatment, a larger scale, placebo-controlled trial is further carried out.

Body composition is determined by the following procedures:

(1) Anthropometric measurements: the skin thickness from the triceps subscapular, suprailiac and thigh is measured using Lange calipers. Waist:hip ratios are measured by a tape;

(2) Estimation of total body fat using MRI: multiple axial images from the level of the aortic bifurcation (L5), and mid-thigh are taken using magnetic resonance imaging to determine subcutaneous and deeper fat depots in study subjects. A 3 Tessla magnet is used (General Electronics, Milwaukee, Wis.). A computer program is used to integrate the amount of fat mass seen in these images (Fowler et al., *Am. J. Clin. Nutr.* 56:7-13, 1992). For this, MEDx image analysis software package (Medical Numerics, Sterling, Va.) is used. The following parameters are collected: total visceral fat volume, total abdominal subcutaneous fat volume, and total thigh subcutaneous fat volume; (3) MRI of the liver: all enrolled patients have a baseline MRI of the liver to evaluate liver volume (Fowler et al., supra); and (4) DEXA (Dual X-ray absorptiometry) scan for total body composition: this involves using a dual X-ray absorptiometer (Hologic Inc., Bedford, Mass.) for estimation of fat and lean body mass; its validity has been shown in multiple studies with various groups of patients (Haarbo et al., *Clin. Physiol.* 11:331-341, 1991).

Metabolic evaluation of patients with NASH are determined by the following tests:

(1) Confirmation of serum leptin levels and measurement of free leptin levels. Serum leptin levels are collected after an overnight fast and three samples that are drawn 30 minutes apart are averaged to compensate for the pulsatility seen in serum leptin levels. Serum leptin samples are determined using a commercial kit manufactured by Linco Inc. (St. Charles, Mo.). In addition, levels of leptin binding proteins and the circulating form of the ob receptor and free leptin index are determined using commercially available kits from either Linco Inc. (St. Charles, Mo.) or R&D systems (Minneapolis, Minn.);

(2) Baseline blood tests: The following tests are performed after an overnight fast: fasting glucose and insulin, fasting triglycerides, fasting free fatty acids, fasting total HDL and LDL cholesterol, apolipoproteins A and B, serum ALT, AST, GGT, albumin, alkaline phosphatase, bilirubin (direct and indirect), serum electrolytes, BUN and creatinine, and calcium. Approximately 5 mL of serum is put in aliquots and frozen for potential future tests;

(3) Determination of whole body insulin sensitivity using a frequently sampled intravenous glucose tolerance test (Beard et al., *Diabetes* 35:362-369, 1986). After an overnight fast and prior to administration of any medication, this test is performed as previously described. Insulin sensitivity is predicted based on the Minimal Model.

Assessment of energy status is determined using the following protocols:

(1) Assessment of energy intake. Dietary intake is assessed using three-day food records. Subjects are asked to record the type and amount of food and beverage consumed for two consecutive weekdays and one weekend day, using standard household measures (cups, tablespoons, and the like). Trained dieticians review the records with the subjects to clarify recipes, servings, and forgotten foods that were consumed. Food intake data is analyzed and energy and nutrient intake is calculated using the Nutritionist V Diet Analysis software (First Data Bank Inc., San Bruno, Calif.);

(2) Resting energy expenditure (REE) is measured prior to the intravenous glucose tolerance test (IVGTT) after 30 minutes of rest. The test is carried out using a microprocessor-controlled indirect calorimetry device (Sensormedics, Yorba Linda, Calif.) that measures oxygen consumption and carbon dioxide production (Sparti et al., *Metabolism* 46:1225-1230, 1997). The procedure involves positioning a canopy over the patient's head that allows the patient to exchange gas only from a chamber containing 21% oxygen and 0.4% carbon dioxide. The recording is carried out for at least 20 minutes after achieving a steady curve. This measurement is done under conditions of minimal physical activity. The amount of carbon dioxide generated and oxygen consumed by the patient is determined by the microprocessor; and (3) Validity of data for energy status. Subjects with ongoing weight loss are excluded; thus, energy intake and energy expenditure should be roughly the same, ensuring the validity of the food intake data.

Determination of circulating levels of other adipokines implicated in liver metabolism or liver injury: Fasting plasma samples are collected and stored for determination of adiponectin, tumor necrosis factor-alpha (TNF-α) and interleukin 6 (IL-6) levels. Adiponectin is measured as previously described using a commercially available kit by Linco Inc (St. Charles, Mo.) (Gavrila et al., *J. Clin. Endocrinol. Metab.* 88:4823-4831, 2003). IL-6 and TNF-α levels are measured with a "Quantikine" Enzyme-Linked Immunosorbent Assay (ELISA) (R&D Systems, Minneapolis, Minn.). The inter- and intra-assay coefficients of variation and the detection limits are, respectively, 7.2%, 7.8%, and 0.156 pg/mL for IL-6; and 12.6%, 5.9%, and 0.5 pg/mL for TNF-α. Samples also are collected and stored for determination of concentrations of TNF-α soluble receptor, TGF-β and resistin.

In order to understand the pathways by which leptin's effects are mediated, the circulating levels of hormones implicated in appetite and weight regulation, and potentially affected by leptin, are determined. For example, gastrointestinal peptides and hormonal targets of leptin (i.e., ghrelin, glucagon-like peptide-1 (GLP-1), peptide YY (PYY), pancreatic polypeptide, cholecystokynin, cortisol, and melanocortins) are measured. These polypeptides and hormones are measured using standardized commercially available kits (LINCO Research Inc, St. Charles, Mo.).

As discussed previously herein, treatment with recombinant leptin is expected to increase mean leptin concentration from 6 ng/mL to 15 ng/mL after only one month of treatment. Subjects treated with recombinant leptin are expected to show decreased level of steatosis on histological examination and decreased liver volumes on MRI. It is also expected that subjects show significant decreases in mean total NASH scores as well as decreases in scores of fibrosis and inflammation. In addition, it is expected that subjects show improvement in metabolic parameters such as insulin resistance and hypertriglyceridemia. The positive effects of exogenous leptin therapy are expected to have a significant long-term impact on the patients' quality of life.

Example 5

Determining the Mechanisms of Leptin's Role in NASH

To investigate the mechanisms by which leptin is involved in the pathology of NASH, the following experiments are carried out. The goal of this set of experiments is to determine whether a consistent pattern of changes in selected genes can be identified in those individuals with the different levels of leptin at baseline, and whether leptin therapy has an effect on alterations in the expression of the selected genes.

Studies in leptin-deficient rodents have identified a set of genes that appear to be specifically modulated by leptin administration (Cohen et al., *Science* 297:240-243, 2002). Using these genes as a starting point, quantitative, real-time reverse transcription PCR (qRT-PCR) is carried out on mRNA from liver biopsy samples obtained from subjects at baseline (before leptin treatment) and after 12 months of recombinant leptin therapy. The expression of SCD-1, SCD-2 and SCD-4, glucose-6-phosphatases, malate NADP oxidoreductase, Spot14, ATP citrate lyase, and fructose bisphosphatase are carried out. Many of these genes are thought to be regulated by leptin and not by weight loss (Cohen et al., supra, 2002). The genes shown in FIG. 3 are also examined, as preliminary studies have identified the expression of these genes to be significantly changed in the face of hepatic steatosis.

RNA from liver biopsy samples is isolated using a Quiagen RNeasy kit followed by treatment with RNase-free DNase (Ambion). To assess the expression of the individual genes, an aliquot (2 μg) of total RNA is reverse-transcribed to generate single-strand cDNA. Real time PCR is carried out using an Opticon Cycler (MJ Research) using conditions specific for each primer set. Two microliters of cDNA is amplified in a final volume of 25 μL using the Quiagen CyberGreen Quantitec system. After an initial denaturation (95° C. for 15 min) amplification is carried out for approximately 35 cycles. The amplification of 18s RNA is used to normalize each sample for reverse transcription (RT) efficiency. In general, each primer set is chosen to amplify a 3' domain of the mRNA of interest and, where possible, the PCR product crosses a predicted intron to examine the genomic contamination of the PCR reaction. Duplicate samples of RNA from each biopsy are individually quantified.

Because leptin therapy may induce a reduction in food intake and this reduction in food intake can subsequently result in weight loss, patients are monitored for an additional six months after discontinuation of leptin. While data from rodent models indicates that leptin's effects on glucose and lipid metabolism are distinct from its effects on energy intake, there is very limited human data regarding differential effects of leptin on these two distinctive processes. Furthermore, recent rodent data suggest that the effects of leptin on energy intake can be uncoupled from its effects on glucose metabolism in the liver via interfering with specific down-stream messengers (Munzberg et al., *Cell. Mol. Life Sci.* 62:642-652, 2005). Thus, it is important to collect information on whether leptin's effects on food intake can be separated from its effects on metabolic parameters.

Leptin is administered as set out in the Examples above. Within the first three months after leptin therapy, patients are prescribed the same diet that they indicated that they were following during the last 3 months of leptin therapy. The diet plan is formulated based on the food intake data that patients have provided at their 9-month and 1-year visits. Thus, data are analyzed and a diet plan is prescribed. The validity of reported data is assessed with the determination of resting energy expenditure (REE). Roughly, REE should match food intake. Patients are also evaluated at the end of this 3rd month and all follow up studies, except the liver biopsy, are repeated. At that time, food intake is liberalized. Patients are also evaluated after an additional visit 3 months later. Again, all follow-up studies are repeated except for liver biopsy. Results are analyzed using a two-factor analysis of variance (ANOVA) with repeated measures.

Results of these experiments are used to understand the mechanisms by which leptin modulates steatosis and steatohepatitis in the liver. Preliminary data suggests that individuals with NAFLD have an increase in the expression levels of genes associated with lipid and glucose metabolism and a reduction in the expression levels of genes associated with VLDL export (FIG. 3). The present study is particularly interested in changes (i.e., modulation) in gene expression in those genes playing a role in lipogenesis and lipid oxidation. It is hypothesized that there is a decreased expression of genes associated with lipogenesis and an increased expression of genes involved in lipid oxidation. Subjects are expected to show similar changes as well as increases in leptin-regulated' genes (Cohen et al., supra, 2002). If leptin therapy is successful, there is a significant decrease in the expression of leptin-responsive' genes and this decrease in expression of leptin-responsive genes results in the improvement of hepatic steatosis and with improvement in NASH scores.

Because caloric restriction and/or weight loss have been shown to improve serum transaminase levels and metabolic parameters in small groups of patients with NASH after short-term interventions, and recombinant leptin therapy may lead to significant amounts of weight loss, confounding effects have to be considered. To solve this potential experimental design problem, the following two protocols have been devised.

First, subjects undergo an additional follow-up period at the end of the study during which subjects are encouraged to follow the diet they consumed while on leptin therapy for a period of three months. Next, subjects consume an ad libidum diet (i.e., without dietary restrictions) for an additional three-month period. While liver biopsy is not repeated at these time points, clinical, biochemical and imaging studies are repeated to determine whether there are overt changes that would suggest a direct effect of leptin versus diet. Depending on the time course of change in parameters on leptin therapy, this follow-up period may need to be extended to observe significant changes.

Second, data from the subjects is compared to data from other patients in an ongoing study evaluating the effects of both short-term and long-term weight loss on liver histopathology in patients with NASH. It is important to note that current evidence is suggestive of leptin's additional metabolic effects above and beyond its effects on energy intake (Shimomura et al., supra, 1999; Oral et al., supra, 2002; Munzberg et al., supra, 2005). Furthermore, the central signaling pathways downstream of the leptin receptor leading to metabolic effects appear to be different than pathways leading to appetite control. For example, SOC-3 (a downstream target of leptin receptor activation) deficiency in models of obesity (Munzberg et al., supra). results in protection against obesity and overeating, but does not reverse insulin resistance, increased gluconeogenesis, and hepatic fatty deposition. This landmark observation suggests that leptin's effects on food intake may be uncoupled from its effects on the liver and on whole-body insulin sensitivity. The present study has the potential to provide important human data about the divergence of signaling pathways leading to leptin's effects.

If the efficacy of leptin is primarily due to its effects of decreased caloric intake and resultant weight loss, one likely criticism would be that dietary intervention is a cheaper way of inducing these effects without the added discomfort of daily injections of leptin. However, it is important to recognize that rates of adherence to life style modification without the reinforcement of a multi-disciplinary medical team for periods longer than six months are very low. Implementation of this reinforcement may not be less costly than administration of a drug. Further, if the current study provides proof-of-principle, undertaking efforts to make leptin delivery less cumbersome to the patient may be justified.

Messenger RNA levels are examined in the biopsy specimens. In the liver, a wide variety of genes related to both glucose and lipid metabolism are regulated at the translational level, thus changes are detectable, at least in the group that responds to leptin in a clinical manner. However, proteins are the work-horses of the cell and the levels of mRNA may not necessarily predict activity. Thus, an analysis of protein expression is also included in the invention. Western blots for proteins, such as SCD-1, sterol regulatory-element-binding protein-1c (SREBP-1c), and PPAR gamma coactivator 1 alpha (PGC-1α), are also carried out.

Serum samples (both baseline and during an intravenous glucose tolerance test (IVGTT)) and liver biopsy specimen obtained from the patients constitute the study materials. In addition, patients are subject to imaging studies that are used to calculate their body composition. Patients also undergo a metabolic cart study to measure their resting energy expenditure (REE), respiratory quotient (RQ), and their percent fat and carbohydrate oxidation. At the time patients are considered eligible for the study, they will have undergone a liver biopsy.

Example 6

The Effect of Leptin in the Treatment of Fatty Liver and NAFLD

Although the initial clinical trial focuses on the use of leptin in the treatment of NASH, it is contemplated that leptin also provides beneficial effects in the treatment of other diseases or conditions associated with fatty liver. Although simple fat deposition in the liver, without the inflammatory component, is considered benign and non-progressive, there are other conditions such as NAFLD and ALFD which are contemplated for treatment with leptin Likewise, other conditions which are contemplated to benefit from leptin therapy include alpha-1 anti-trypsin deficiency-induced fatty liver disease, parenteral nutrition induced fatty liver disease, simple steatosis associated with overweight and obesity, non-alcoholic and alcoholic steatohepatitis, and steatohepatitis associated with any form of hepatitis, including hepatitis C (HCV).

Thus, the invention includes the use of leptin to decrease fat content in the liver, leading to favorable metabolic effects, such as decreasing insulin resistance. Because increased fat in the liver is a direct cause of insulin resistance, it is expected that leptin therapy will decrease insulin resistance and likewise have beneficial effects in the treatment of NAFLD and possibly even in AFLD.

Thus, the present invention extends the use of leptin therapy in the treatment of various types of fatty liver disease, including NAFLD, AFLD, alpha-1 anti-trypsin deficiency-induced fatty liver disease, parenteral nutrition induced fatty liver disease, simple steatosis associated with overweight and obesity, nonalcoholic and alcoholic steatohepatitis, and steatohepatitis associated with any form of hepatitis, including hepatitis C (HCV).

Example 7

The Effect of Leptin in the Treatment of NASH with RLD after Six Months of Treatment As set out in detail above, recombinant leptin therapy improves insulin sensitivity and dyslipidemia and reverses nonalcoholic steatohepatitis (NASH) in leptin deficient lipodystrophy in humans. Based on these prior observations, experiments were carried out to determine if recombinant leptin therapy is effective in reversing the histopathological changes as well as fat deposition in patients with biopsy proven NASH (NASH activity score 3 or higher with a minimum score of 1 on steatosis, inflammation and hepatocellular injury and/or fibrosis) and relative leptin deficiency (circulating leptin levels<25th percentile of BMI matched controls from NHANES III population).

To date, nine non-diabetic men (age: 32 to 53 years, weight: 77.9 to 106.2 kgs, BMI 26.2 to 31.8 kg/m2, circulating leptin levels 2.7 to 9.0 ng/dL, NASH Activity Score 3 to 11, ALT: 26 to 257 IU/L, ⅞ on lipid lowering therapy with a statin or a fibrate for dyslipidemia, ⅕ on metformin for IGT, ⅔ on antidepressive medications) with intact hepatic synthetic function were enrolled in a pilot efficacy trial. As discussed previously above, no dosing changes are allowed in the cited drugs during the one year study period.

The first eight of these subjects have completed 6 months of recombinant leptin therapy with METRELEPTIN (Amylin Pharmaceuticals, Inc., San Diego, Calif.) given subcutaneously daily at a dose of 0.1 mg/kg/day. As shown in Table 6, body weight and liver fat as measured by MRI and MR spectroscopy (MRS) decreased in 7 of the 8 subjects at the 6-month follow-up.

TABLE 6

Effect of Leptin on Body Weight and Liver Fat

| Subject | Weight Baseline (kg) | Weight 6-months (kg) | Liver Fat Baseline (%) MRI | MRS | Liver Fat 6-months (%) MRI | MRS |
|---|---|---|---|---|---|---|
| NASH-1 | 82.3 | 76.0 | 9 ± 3 | 15 | 7 ± 3 | 9 |
| NASH-2 | 83.8 | 78.7 | 16 ± 4 | 16 | 8 ± 2 | 4 |
| NASH-3 | 106.2 | 106.8 | 32 ± 3 | 29 | 31 ± 3 | 32 |
| NASH-4 | 80.7 | 77.5 | 8 ± 3 | 7 | 5 ± 3 | 4 |
| NASH-5 | 89.0 | 86.9 | 22 ± 3 | 25 | 17 ± 3 | 10 |
| NASH-6 | 99.1 | 96.2 | 22 ± 2 | 23 | 15 ± 3 | 13 |
| NASH-8 | 91.8 | 88.6 | 22 ± 3 | 19 | 14 ± 2 | 11 |
| NASH-10 | 99.9 | 91.2 | 22 ± 3 | 20 | 9 ± 2 | 5 |

Figure 4:
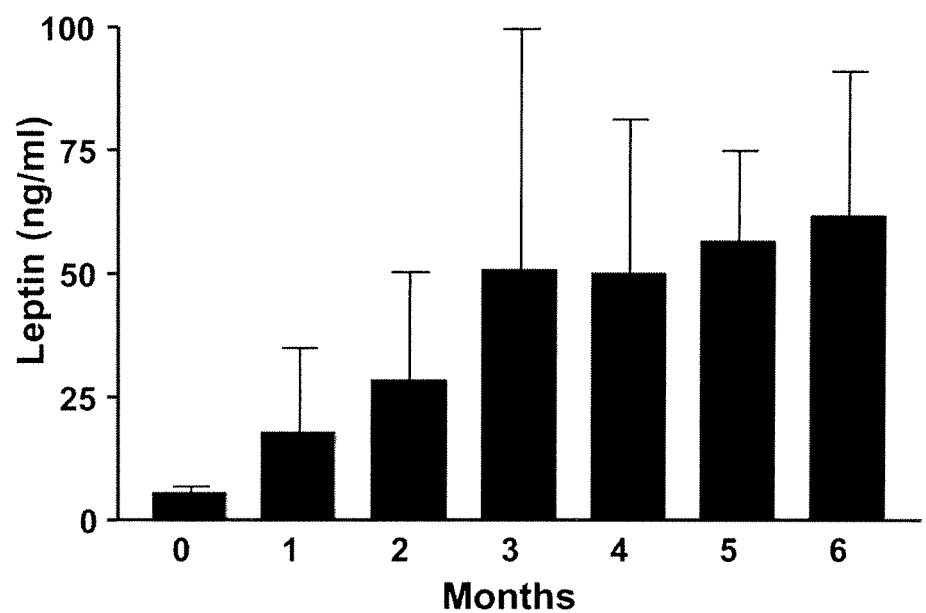
FIG. 4 shows changes over 6 months in serum leptin levels in non-lipodystrophic patients with NASH and RLD who were treated with leptin.
Figure 5:
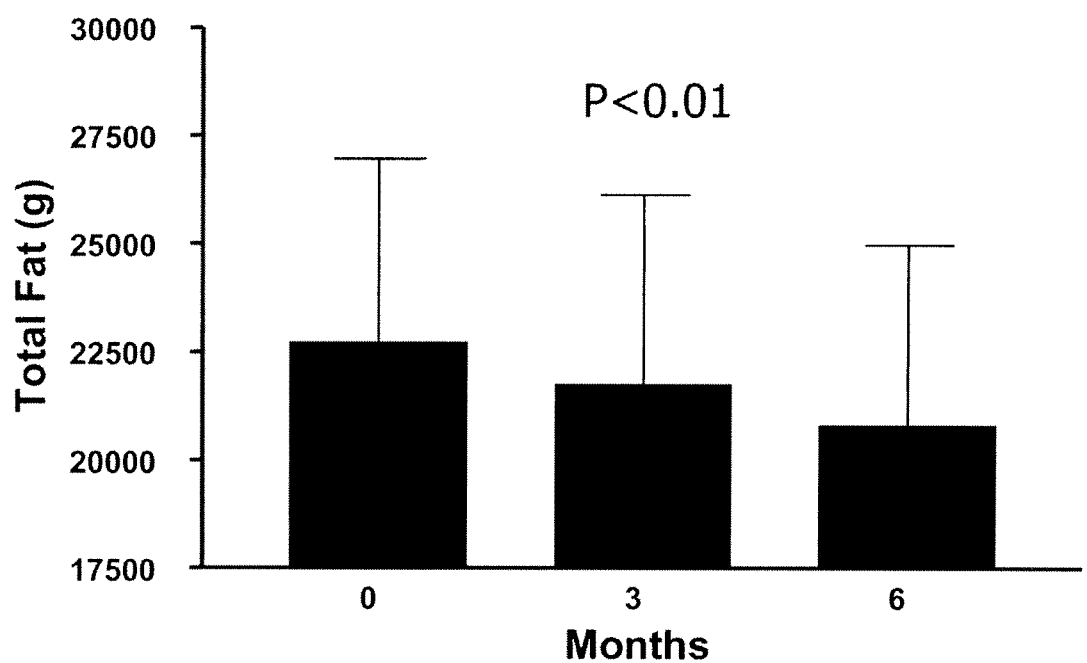
FIG. 5 shows the effect of leptin on fat mass in non-lipodystrophic patients with NASH and RLD who were treated with leptin.
Figure 6:
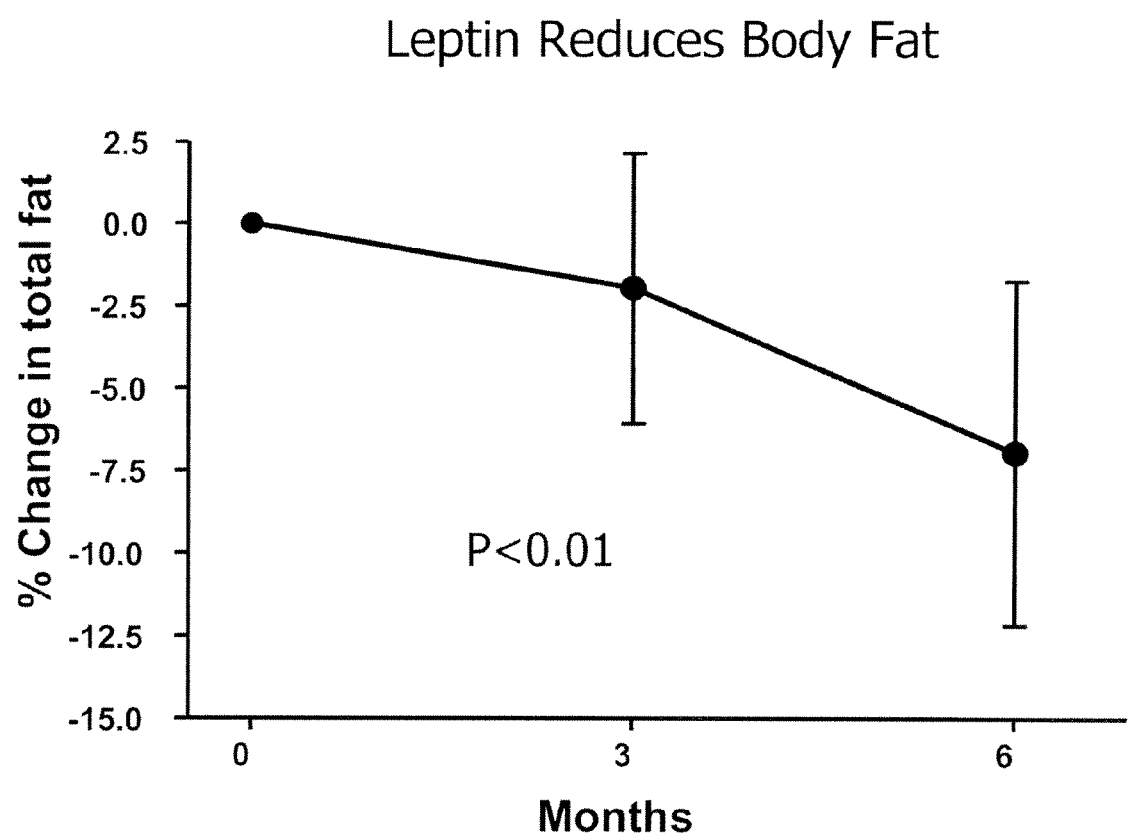
FIG. 6 shows the effect of leptin on body fat in non-lipodystrophic patients with NASH and RLD who were treated with leptin.
Figure 7:
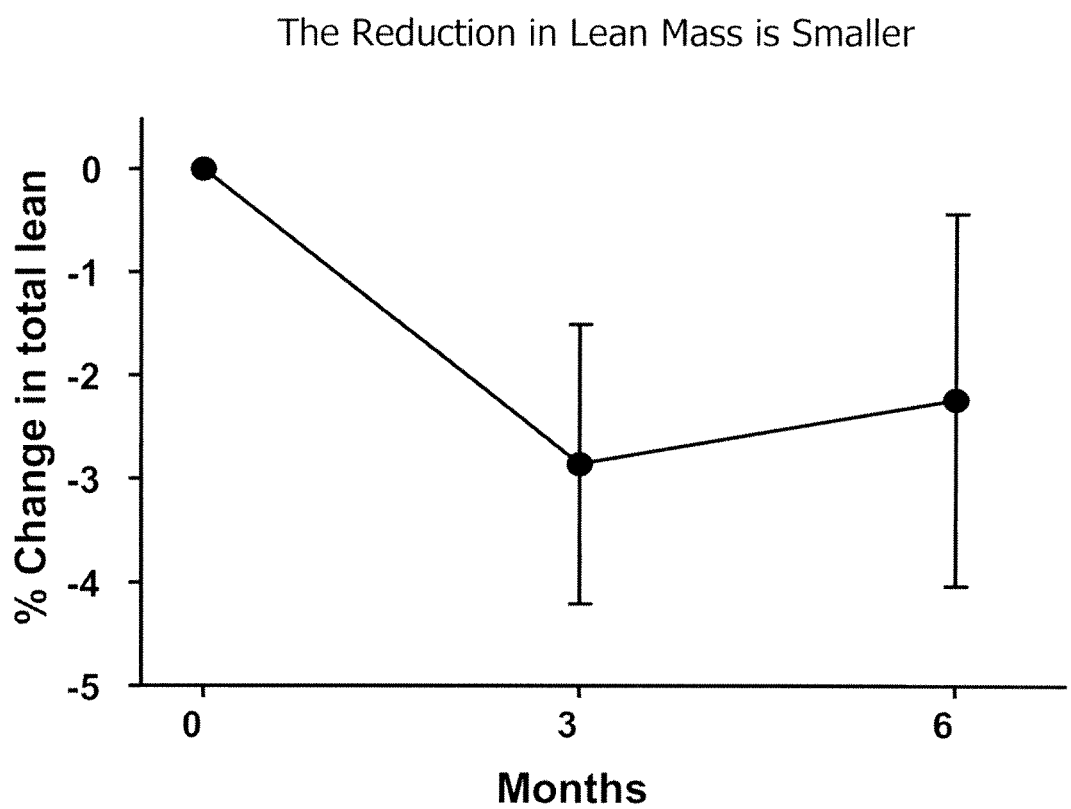
FIG. 7 shows the effect of leptin on lean mass in non-lipodystrophic patients with NASH and RLD who were treated with leptin.
Figure 8:
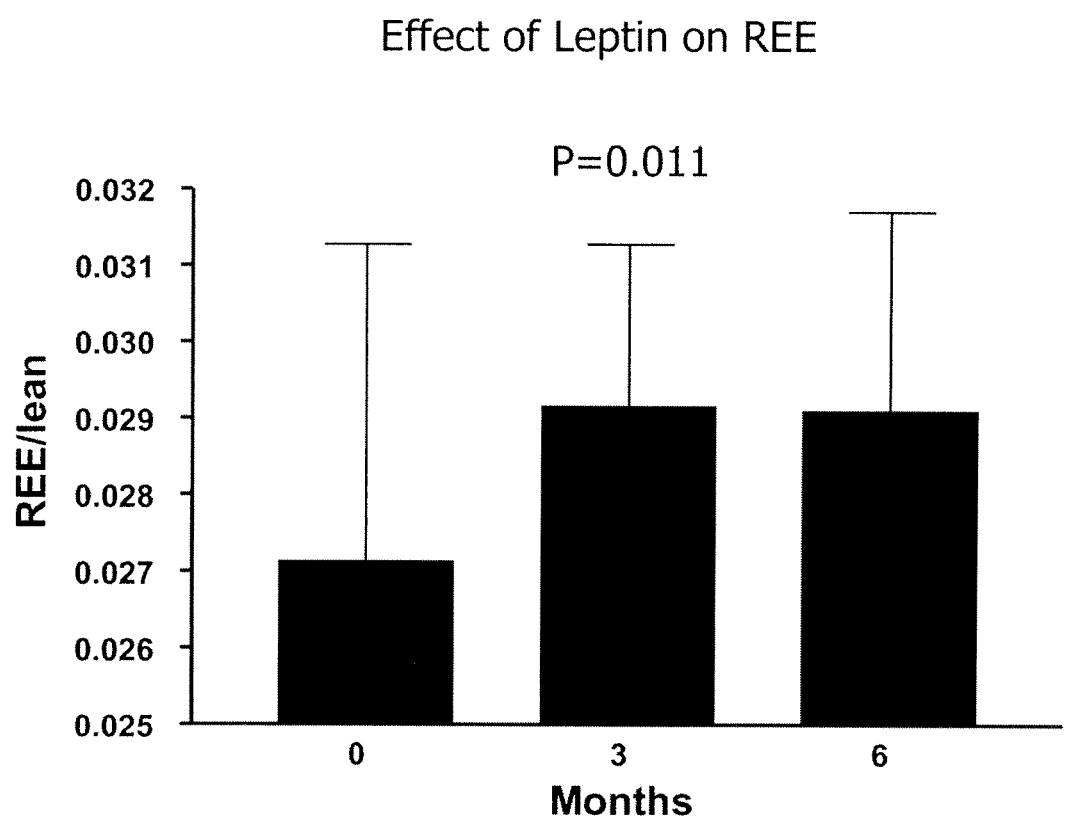
FIGS. 8 and 9 show the effect of leptin on REE in non-lipodystrophic patients with NASH and RLD who were treated with leptin.
Figure 9:
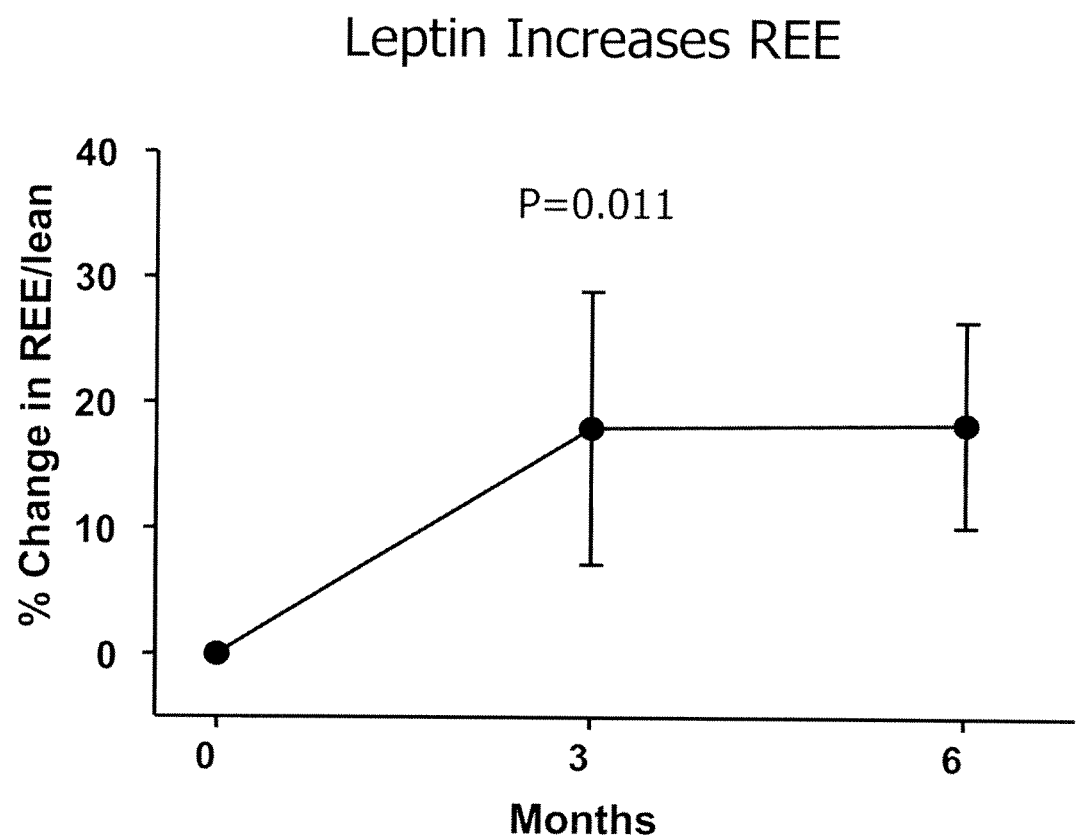
Figure 10:
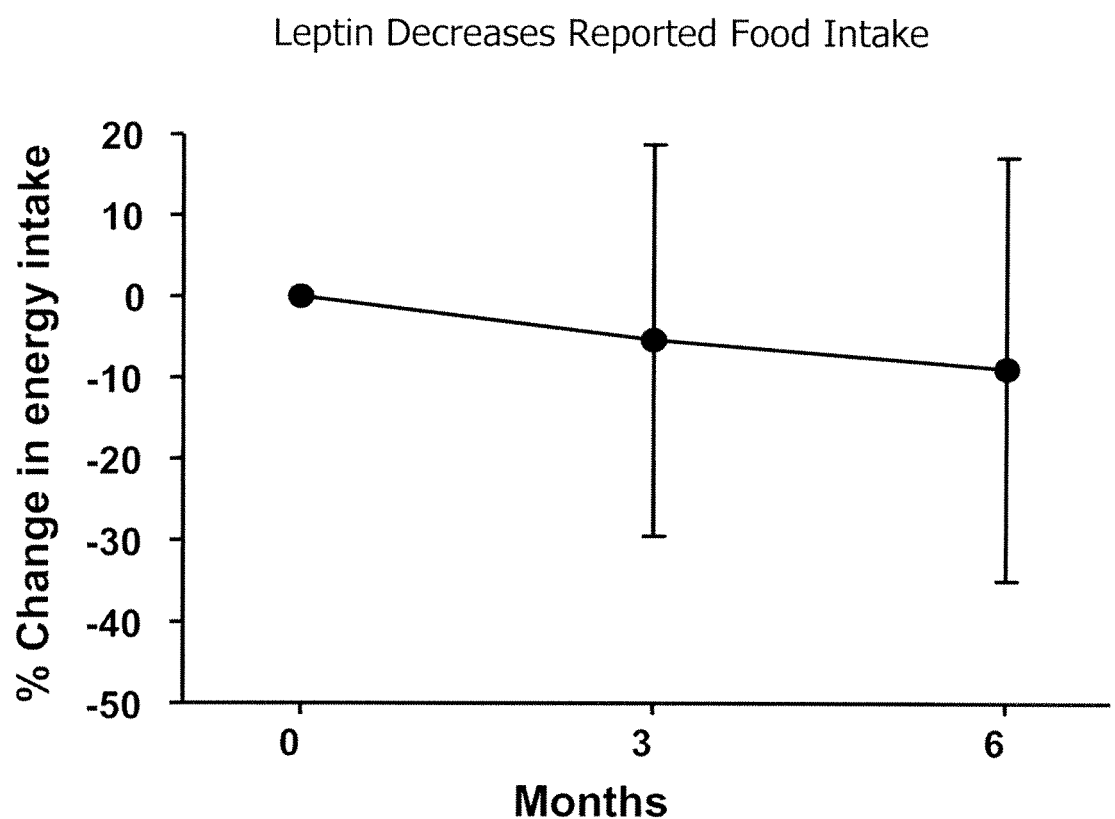
FIG. 10 shows the effect of leptin on food intake in non-lipodystrophic patients with NASH and RLD who were treated with leptin.
Figure 11:
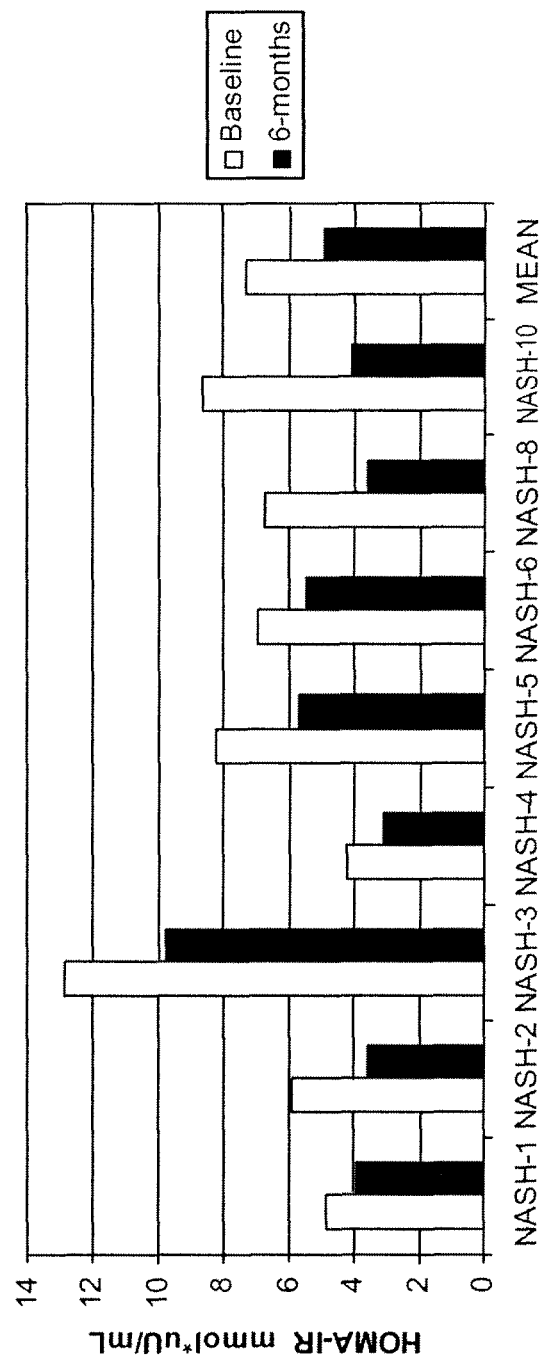
FIG. 11 shows the effect of leptin on insulin sensitivity in non-lipodystrophic patients with NASH and RLD who were treated with leptin.
Figure 12:
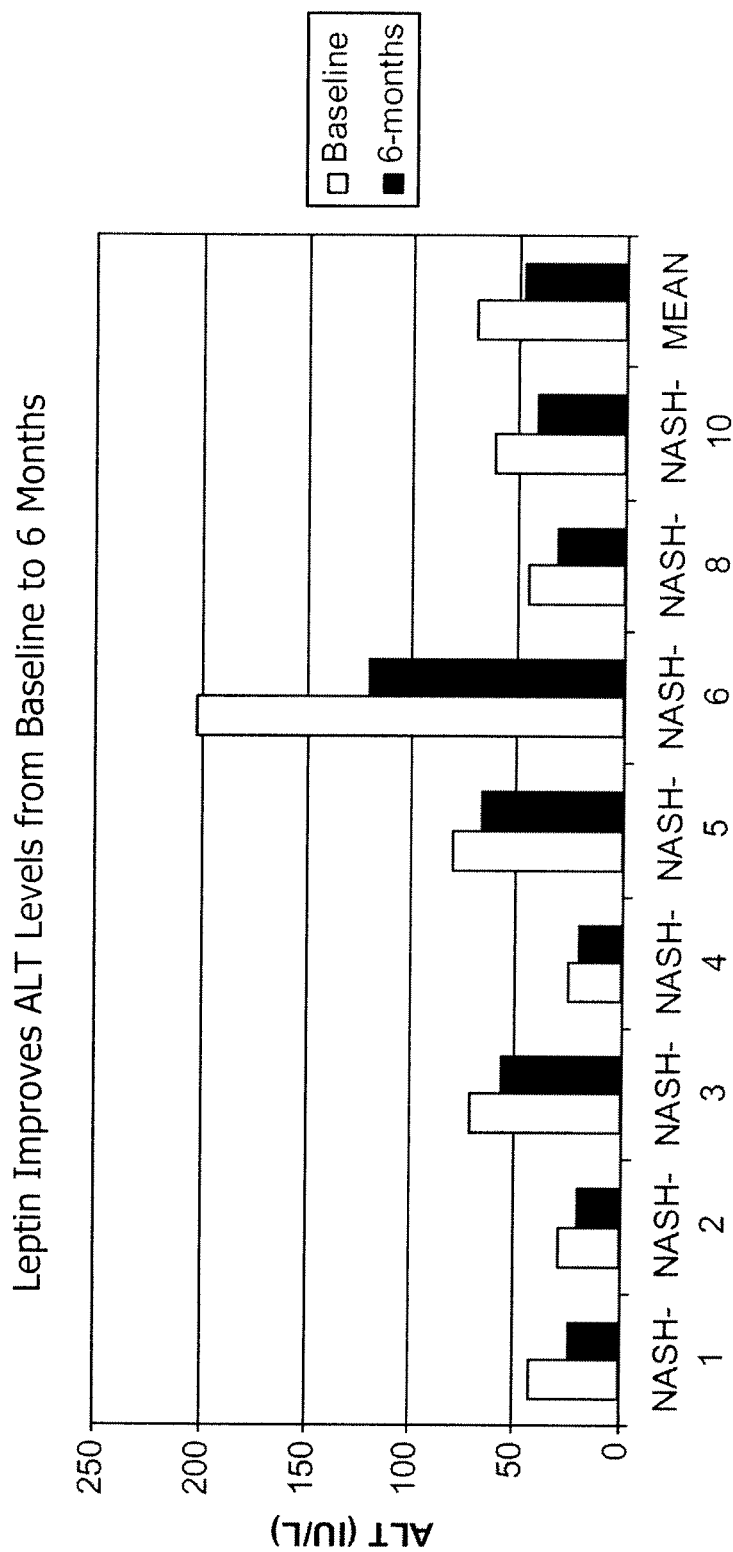
FIG. 12 shows the effect of leptin on ALT in non-lipodystrophic patients with NASH and RLD who were treated with leptin.

High physiological levels of leptin were achieved (FIG. 4). Patients lost weight, predominantly due to the loss of body fat and liver fat (Table 6; FIGS. 5-7). There were increases in REE/Total Lean Mass (FIGS. 8 and 9) and decreases in caloric intake (FIG. 10). Moreover, there were favorable effects on insulin sensitivity (FIG. 11) and ALT levels (FIG. 12). There were no detectable changes on triglycerides, total and unesterified FFA profiles and measured serum desaturation indices (data not shown).

Figure 13:
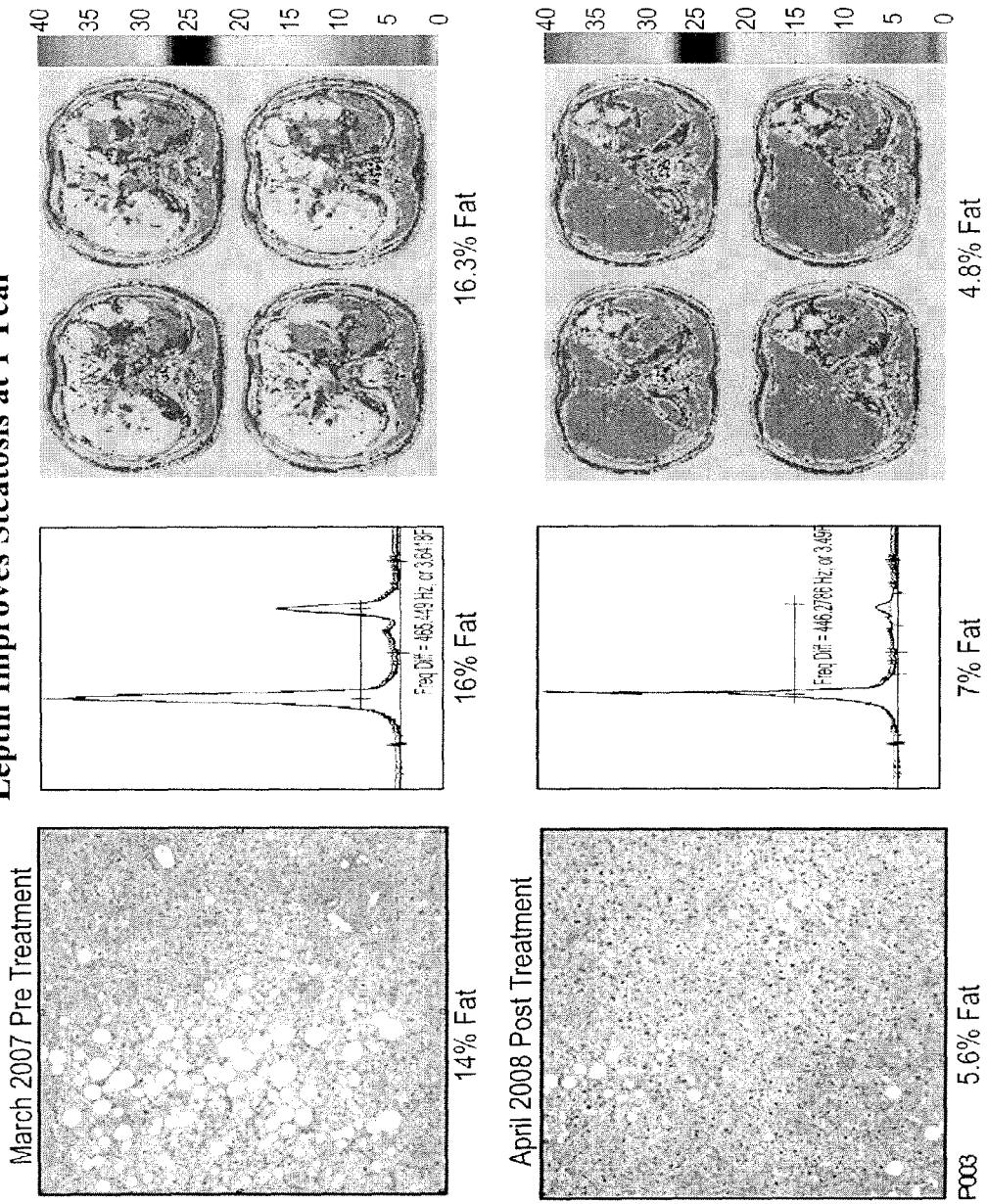
FIG. 13 shows that leptin improves steatosis at 1 year of treatment.

Respective data from one patient along with liver MRI/MRS results are shown in FIG. 13. A predominant effect of treatment was on steatosis score, but there were improvements in inflammation and hepatic injury scores in one patient (data not shown). There was no worsening in inflammation or fibrosis (data not shown) scores as implicated from previous in vitro or rodent studies.

All subjects underwent a liver biopsy at baseline and are expected to undergo another liver biopsy at 12 months of the study. One subject who completed 12 months of therapy had a reduction of his NASH score from 6 to 3. Overall, recombinant leptin therapy was well-tolerated: ⅔ subjects experienced transient injection site reactions (starting around 3 weeks and subsiding within 4 weeks). Results indicate that a subset of patients with NASH with lower leptin levels at baseline benefit from leptin therapy for weight reduction as well as improvement in hepatic fat content and in hepatic steatosis. These results also indicate that the therapeutic window for leptin may be wider than just absolute leptin deficiency.

Example 8

The Effect of Leptin in the Treatment of NASH with RLD After Over 12 Months of Treatment As set out in Example 8, experiments were carried out to determine if recombinant leptin therapy is effective in reversing the histopathological changes as well as fat deposition in patients with biopsy proven NASH (NASH activity score 3 or higher with a minimum score of 1 on steatosis, inflammation and hepatocellular injury and/or fibrosis) and relative leptin deficiency (circulating leptin levels<25th percentile of BMI matched controls from NHANES III population).

Nine subjects (non-diabetic men, age: 32 to 53 years, weight: 77.9 to 106.2 kgs, BMI 26.2 to 31.8 kg/m2, circulating leptin levels 2.7 to 8.1 ng/dL, total NASH score 3 to 11, ALT: 26 to 257 IU/L, ⅞ on lipid lowering therapy with a statin or a fibrate for dyslipidemia, ⅑ on metformin for IGT, ⅔ on antidepressive medications) with intact hepatic synthetic function were enrolled in an efficacy trial. Seven of these subjects completed >12 months of recombinant leptin therapy (METRELEPTIN, Amylin Pharmaceuticals, San Diego, Calif.) given subcutaneously daily at a dose of 0.1 mg/kg/day. Body weight and body fat improved (i.e., decreased) after therapy. The ratio of Resting Energy Expenditure (REE) to lean mass in kg (REE/Lean) increased and Respiratory Quotient (RQ) decreased. Resting energy expenditure represents the amount of calories required for a 24-hour period by the body during a non-active period. The increase in REE remained stable for the year of therapy indicating that leptin has the effect of increasing metabolic activity or metabolic rate. The change in REE was noticeable beginning at three months of therapy. Patients also reported lower food intake, but this did not reach statistical significance especially at the later time points.

Insulin sensitivity improved significantly after one year of therapy. Patients displayed significant improvement in their liver function tests and in hepatic fat content (i.e., decreased liver fat) as measured via MRI. All subjects underwent a liver biopsy at baseline and at 12 months. Five of the seven subjects who completed 12 months of therapy had a minimum of 3 points of reduction of their NASH scores. The mean reduction in the scores from the 7 patients was from 8.3±2.5 to 5.0±1.7 with a range of 1 to 6 points (p<0.0037). In addition to improvement in steatosis in patients with weight loss, there was also significant improvement in inflammation scores, even in patients without weight loss, and no worsening of fibrosis (while even decreased fibrosis in a few patients). These results suggest that the subset of NASH patients with lower circulating leptin levels at baseline may benefit from leptin therapy. These results also suggest the therapeutic utility of leptin extends beyond absolute leptin deficiency to relative leptin deficiency.

Example 9

Figure 14B:
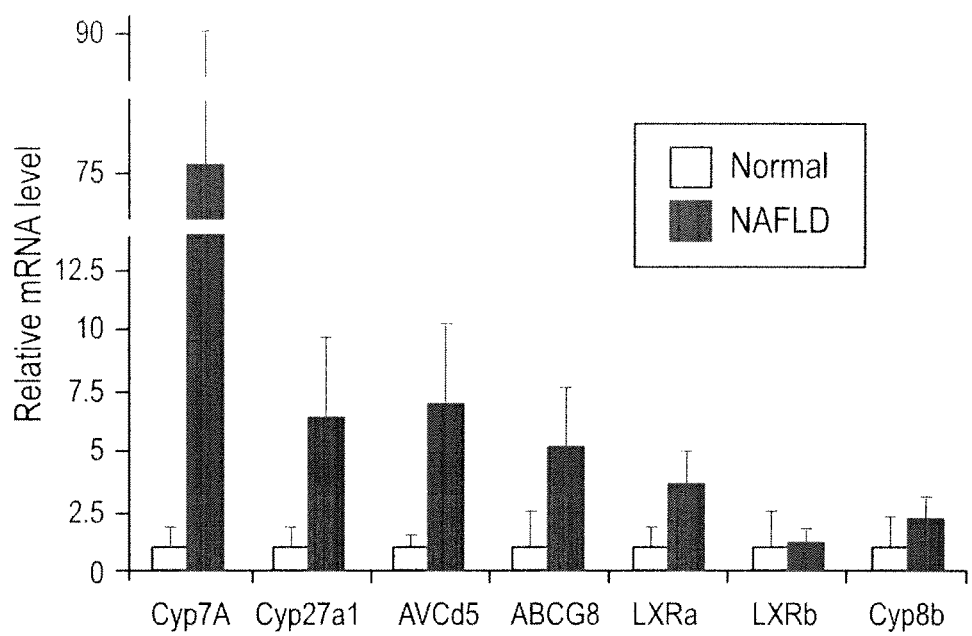
FIG. 14B shows RT-qPCR quantification of mRNAs associated with bile acid synthesis.
Figure 14C:
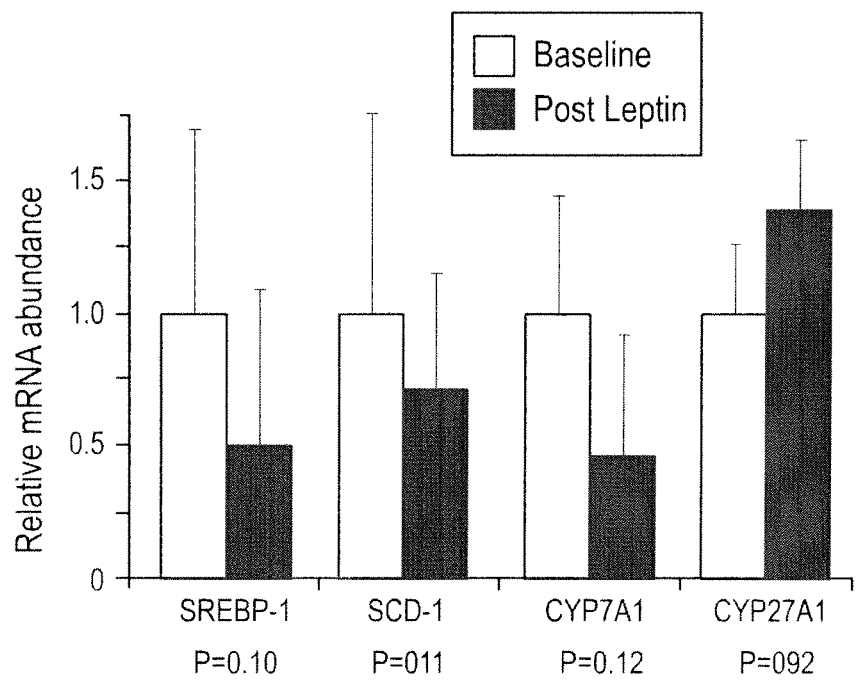
FIG. 14C shows RT-qPCR quantification of indicated mRNA from liver pre- and post-leptin treatment.
Figure 14D:
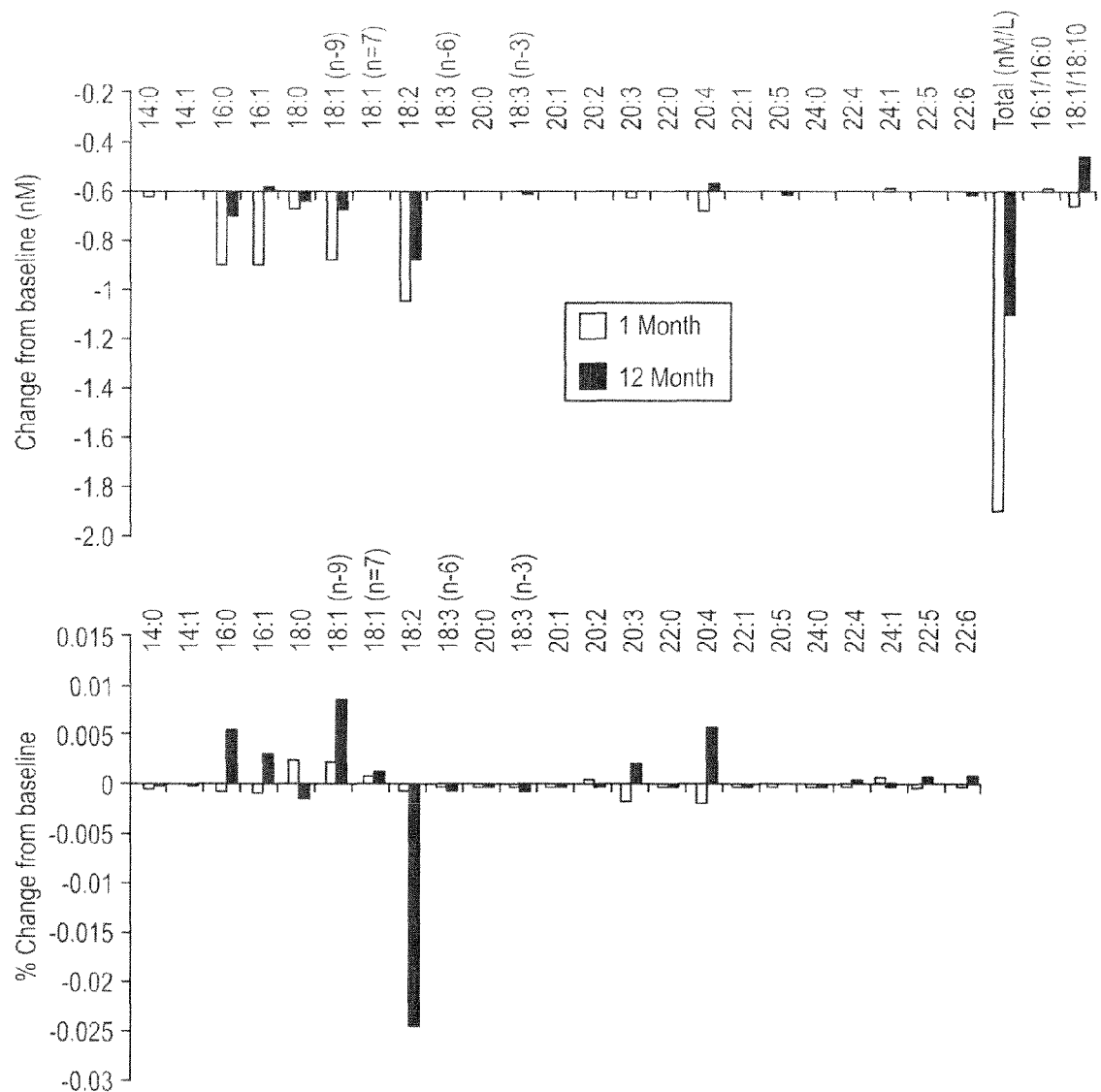
FIG. 14D shows changes in total (top) and relative (bottom) plasma free fatty acid profiles in subjects after either 1 month or 1 year of leptin treatment.

Messenger RNA Profiling of Liver Biopsies in Patients with NASH with RLD after Leptin Therapy The mRNA, isolated from liver biopsies of six patients with NASH with RLD after undergoing leptin therapy, was subject to quantitative profiling using Illumina Biobeads. Differentially expressed genes were identified by paired t-test analysis of expression data. Differentially expressed genes (n=872) were analyzed by Ingenuity Pathway Analysis (Ingenuity Systems, Redwood City, Calif.). The top 10 cannonical pathways identified by Ingenuity Pathway Analysis of mRNA profiles of the liver biopsies are shown in FIG. 14A. RT-qPCR quantification of mRNAs associated with bile acid synthesis are shown in FIG. 14B. RT-qPCR quantification of indicated mRNA from liver pre- and post-leptin treatment are shown in FIG. 14C. Changes in total (FIG. 14D, top) and relative (FIG. 14D, bottom) plasma free fatty acid profiles in subjects after either 1 month or 1 year of leptin treatment are shown in FIG. 14D.

All of the indicated genes were upregulated following treatment with leptin. VEGF, insulin and nitric oxide signaling pathways have similar members which are involved in hormone signaling and indicate a possible improvement in insulin signaling. There were increases also in farnesoid X receptor/retinoid X receptor (FXR/RXR) signaling, which previously has been associated with insulin resistance. After assessing the mRNA levels in liver of normal individuals and those with NAFLD (n=10 each), marked increases in the bile acid synthetic genes (cholesterol 7-hydroxylase (CYP7A1), sterol 27-hydroxylase (CYP27A1), and AVCd5) were identified (FIG. 14B), which was in contrast to the decreased expression of these genes found by others previously. There was also an increase in mRNA levels of the cholesterol transport protein ATP-binding cassette, sub-family G (WHITE), member 8 (sterolin 2 or ABCG8) and in liver X receptor-alpha and -beta (LXRα and LXRβ) (FIG. 14B), similar to that seen previously in insulin-resistant mouse liver. As compared to pre-treatment, treatment with leptin showed a decrease in CYP7A1 mRNA and no change in CYP27A1 (FIG. 14C). Overall, the profiling results on a small number of subjects are consistent with an increase in insulin signaling. Enhanced FXR signaling may indicate leptin-mediated increases in hepatic insulin sensitivity.

The mRNA levels of two genes (sterol regulatory element binding protein 1 (SREBP-1), and stearoyl-coenzyme A desaturase 1 (SCD-1), previously identified as being regulated by leptin in the mouse, were assessed. SREBP-1 is a transcription factor that regulates a number of genes associated with de novo lipogenesis, including SCD-1 which causes the monodesaturation of palmitic and stearic acid. There was a large decrease in SREBP1 mRNA levels and a small, non-significant decrease in SCD-1 levels (FIG. 14C). Assessment of fatty acids derived from total lipids in the peripheral plasma of subjects at 1 and 12 months of leptin treatment showed decreases in total fatty acid content at 1 and 12 months (FIG. 14D, top) and concomitant decreases in 16:1 and 18:1 fatty acids. There were minimal changes in the 16:1/16:0 and 18:1/18:0 ratios, suggesting that overall, SCD-1 activity was not changed. Interestingly, there were marked decreases in linoleic acid (18:2) concentrations in plasma following leptin treatment. The decreases in linoleic acid may also reflect an improvement in insulin sensitivity.

Example 10

Caloric Intake is Reduced in Patients with NASH with RLD After Leptin Therapy

Patients reported approximately a 15% reduction in food intake after 1 year of therapy with leptin. Mean caloric intake per patient was 2400 calories/day at baseline. There was a greater reduction earlier in the course of leptin therapy, after around three to six months of treatment, and then a slight increase in reported food intake. However, the average reported caloric intake while on leptin ranged between 1800 to 2100 calories. This data suggests that leptin has a role in reducing caloric intake in addition to its role in increasing REE.

Although early studies indicate that leptin has a role in reducing caloric intake, additional long term studies are carried out to determine the metabolic effects of leptin. A 1 year, double-blind, randomized study is being carried out to assess the metabolic effects of recombinant leptin or placebo in combination with a moderate caloric restriction in 40 men prospectively identified to have low serum leptin levels. The primary outcome measures are body weight, hepatic fat content by MRI and total NASH scores. Body composition, triglyceride and free fatty acid levels, and insulin sensitivity are also measured. Metabolic parameters following drug withdrawal, while maintaining a fixed caloric diet, are tested to objectively assess the impact of leptin on body weight and hepatic steatosis while controlling for dietary changes. Subjects are tested initially at 3 month intervals for 12 months and then yearly thereafter up to 3 years.

Numerous modifications and variations in the invention as set forth in the above illustrative examples are expected to occur to those skilled in the art. Therefore, it is intended that the appended claims cover all such equivalent variations which come within the scope of the invention as claimed.

What is claimed:

1. A method of treating a fatty liver condition in a non-lipodystrophic subject comprising administering a composition comprising leptin in an amount effective to treat the condition in the subject.

2. The method of claim 1, wherein the subject has a relative leptin deficiency.

3. The method of claim 1, wherein the fatty liver condition is nonalcoholic steatohepatitis (NASH).

4. The method of claim 3, wherein the NASH score improves or decreases.

5. The method of claim 3, wherein fasting serum triglyceride level decreases.

6. The method of claim 1, wherein the fatty liver condition is nonalcoholic fatty liver disease (NAFLD).

7. A method of improving hepatitic steatosis in a non-lipodystrophic subject comprising administering a composition comprising leptin in an amount effective to improve hepatitic steatosis in the subject.

8. The method of claim 1 or 7, wherein administering leptin decreases liver fibrosis or scarring in the subject.

9. The method of claim 1 or 7, wherein administering leptin decreases liver inflammation in the subject.

10. The method of claim 1 or 7, wherein administering leptin decreases liver fat in the subject.

* * * * *